United States Patent
Ghiggeri et al.

(10) Patent No.: US 10,620,201 B2
(45) Date of Patent: Apr. 14, 2020

(54) IN VITRO METHOD FOR PREDICTING, DIAGNOSING AND MONITORING IN THERAPEUTIC FOLLOW UP LUPUS NEPHRITIS

(71) Applicant: PAD 4 DI MARIA ADELE SILVIA DENEGRI S.A.S., Chivari (IT)

(72) Inventors: Gian Marco Ghiggeri, Chiavari (IT); Luca Ghiggeri, Chiavari (IT)

(73) Assignee: PAD 4 DI MARIA ADELE SILVIA DENEGRI S.A.S., Chiavari (IT)

( * ) Notice: Subject to any disclaimer, the term of this patent is extended or adjusted under 35 U.S.C. 154(b) by 419 days.

(21) Appl. No.: 15/112,804

(22) PCT Filed: Jan. 19, 2015

(86) PCT No.: PCT/IB2015/050388
§ 371 (c)(1),
(2) Date: Jul. 20, 2016

(87) PCT Pub. No.: WO2015/107501
PCT Pub. Date: Jul. 23, 2015

(65) Prior Publication Data
US 2016/0349254 A1    Dec. 1, 2016

(30) Foreign Application Priority Data
Jan. 20, 2014   (IT) .............................. RM2014A0027

(51) Int. Cl.
| | | |
|---|---|---|
| *G01N 31/00* | (2006.01) | |
| *G01N 33/53* | (2006.01) | |
| *G01N 33/564* | (2006.01) | |
| *G01N 33/68* | (2006.01) | |

(52) U.S. Cl.
CPC ....... *G01N 33/564* (2013.01); *G01N 33/6854* (2013.01); *G01N 2800/104* (2013.01); *G01N 2800/56* (2013.01)

(58) Field of Classification Search
None
See application file for complete search history.

(56) References Cited

PUBLICATIONS

Bijl et al. (Rheumatology 2002; 41; pp. 62-67).*
Kurien et al. (Scandinavian Journal of Immunology, 2006, 64, pp. 227-235).*
Tascilar et al. (Annals of Oncology 10,Suppl. 4:S107-S110, 1999).*
Tockman et al. (Cancer Research 52:2711s-2718s, 1992).*
Int'l Search Report for PCT/IB2015/050388, three pages (Mar. 2015).
Written Opinion of the ISA for PCT/IB2015/050388, three pages (Mar. 2015).
Grootscholten et al. "Deposition of nucleosomal antigens (histones and DNA) in the epidermal basement membrane in human lupus nephritis" *Arthritis & Rheumatism*, vol. 48, No. 5, pp. 1355-1362 (May 2003).
Li et al. "Biomarker profiling for lupus nephritis" *Genomics, Proteomics & Bioinformatics*, vol. 11, No. 3, pp. 158-165 (Jun. 2013).
Qi-Ying et al. "Anti-C1q antibodies and IgG subclass distribution in sera from Chinese patients with lupus nephritis" *Nephrology Dialysis Transplantation*, vol. 24, No. 1, pp. 172-178 (Jan. 2009).
Schmiedeke et al. "Glomerular immune deposits in murine lupus models may contain histones" *Clinical and Experimental Immunology*, vol. 90, No. 3, pp. 453-458 (Jan. 1992).
Soo et al. "Differential diagnosis of lupus and primary membranous nephropathies by IgG subclass analysis" *Clinical Journal of the American Society of Nephrology*, vol. 7, No. 12, pp. 1947-1955 (Dec. 2012).

\* cited by examiner

*Primary Examiner* — Lisa V Cook
(74) *Attorney, Agent, or Firm* — Sterne, Kessler, Goldstein & Fox P.L.L.C.

(57) ABSTRACT

The present invention relates to an in vitro method for the prediction and/or diagnose of lupus nephritis in subjects affected or potentially affected by systemic lupus erythematosus, an in vitro method for monitoring a therapy against lupus nephritis in subjects affected or potentially affected by systemic lupus erythematosus and a kit for the prediction of the progression of lupus nephritis and/or for monitoring a therapy against lupus nephritis in subjects affected or potentially affected by lupus erythematosus.

8 Claims, 30 Drawing Sheets

IgCs in the glomerular eluates of patients with lupus
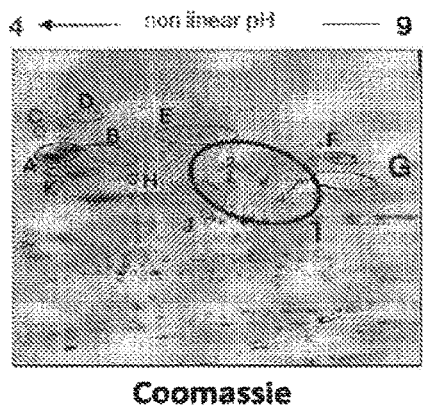
FIG. 1A Coomassie
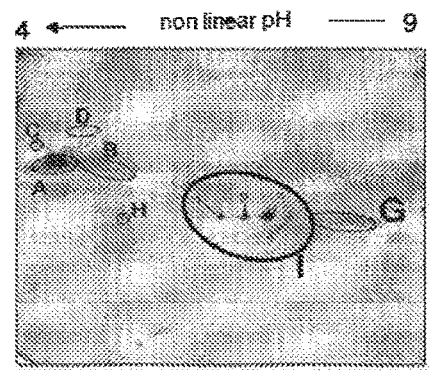
FIG. 1B Class III
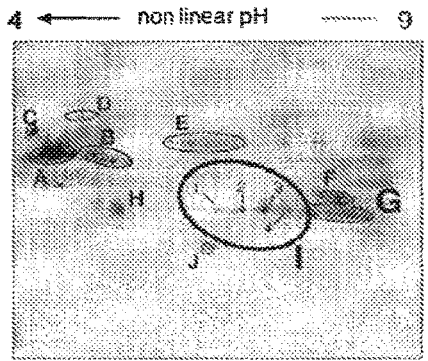
FIG. 1C Class IV
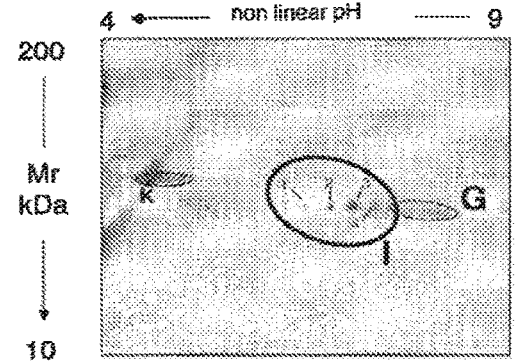
FIG. 1D Class V

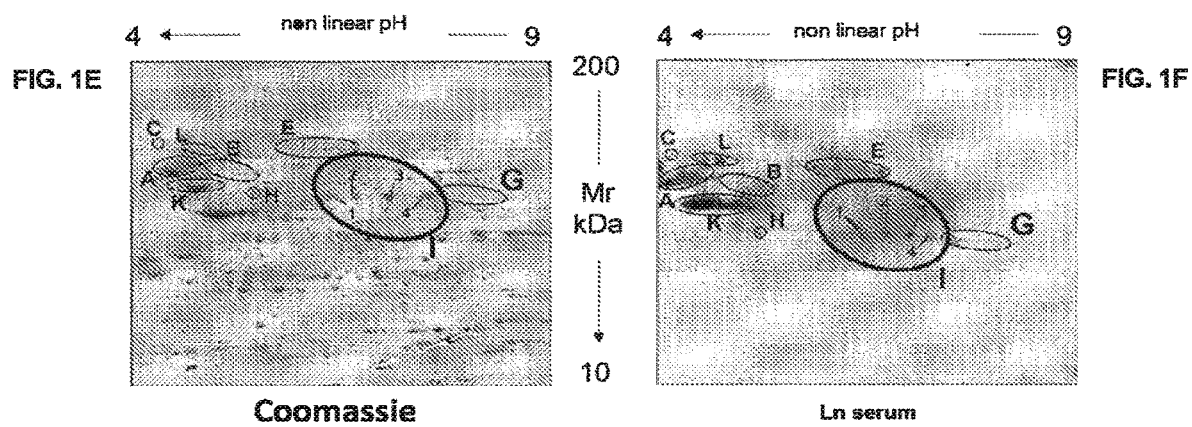

Anti-DNA antibodies in the glomerular

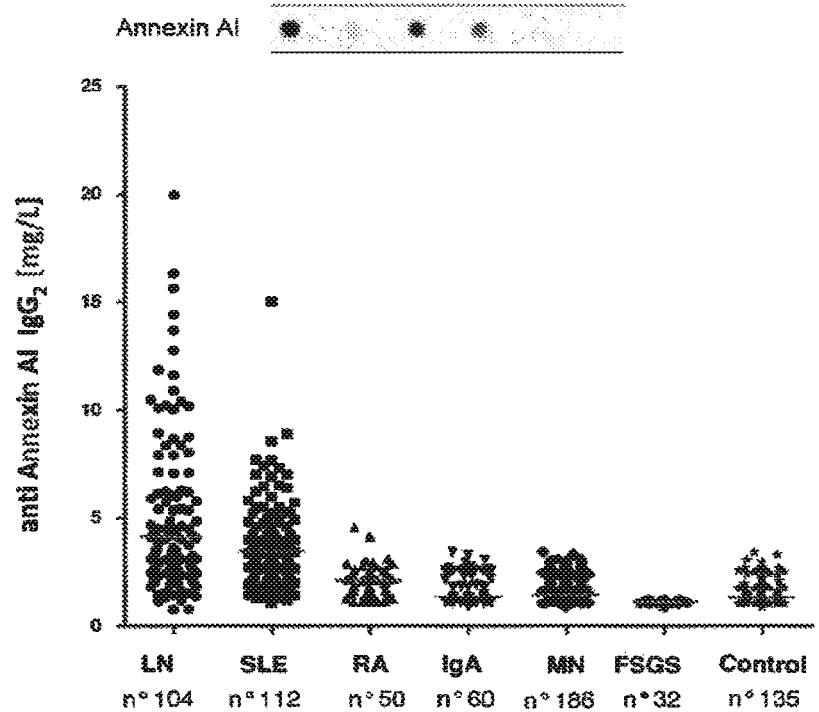

FIG. 6A
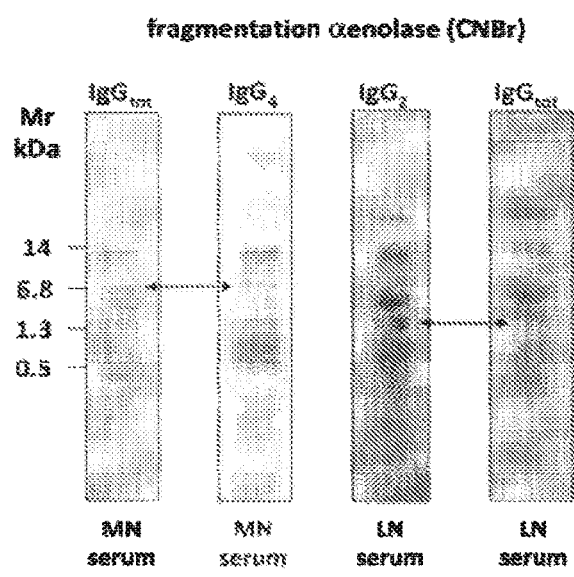
FIG. 6B
LN
IgG$_2$
FIG. 6C
MN
IgG$_4$

FIG. 6D
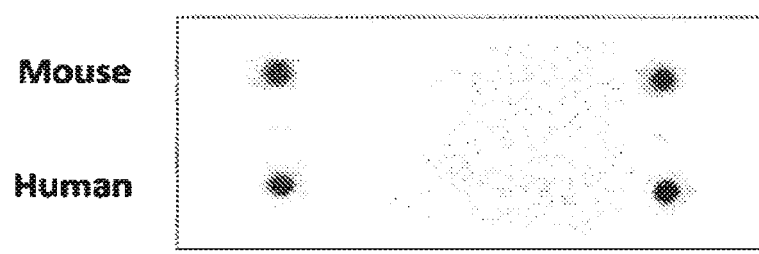
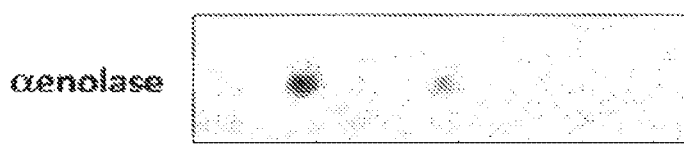

FIG. 10B
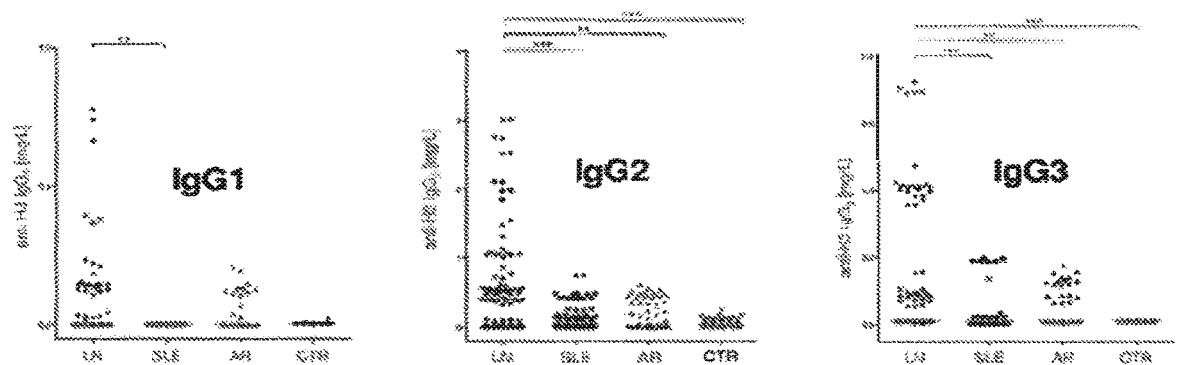
Anti-H3 Ab
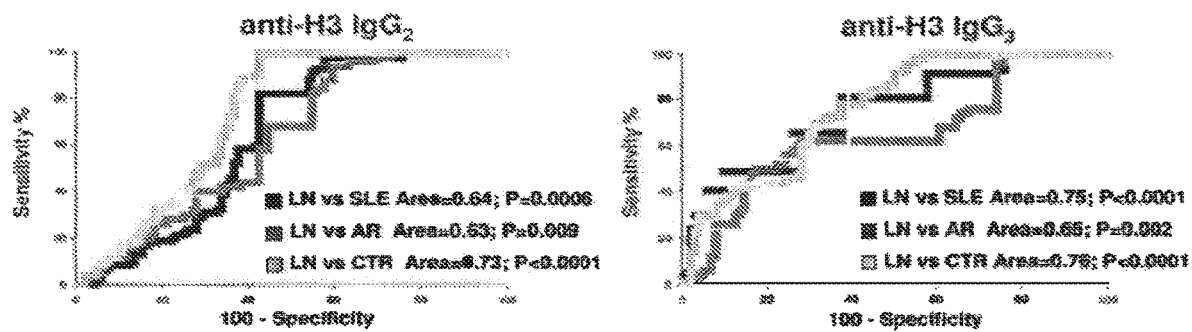

FIG. 10C
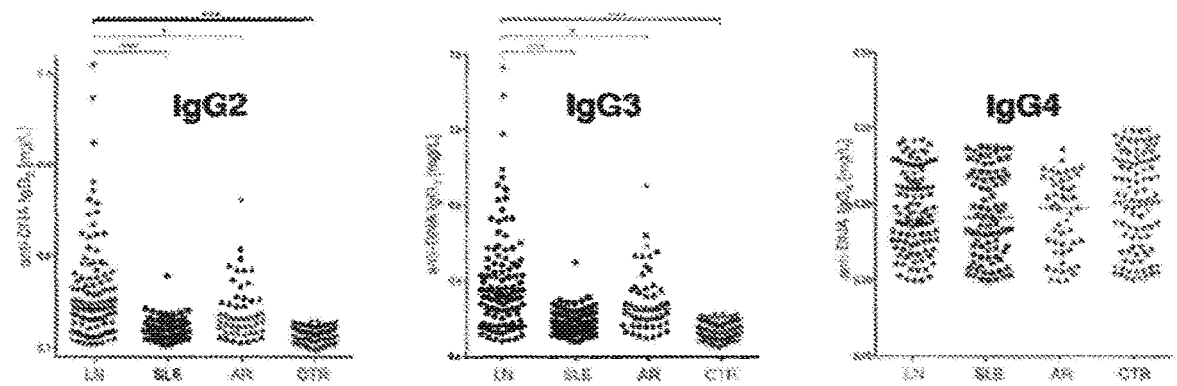
Anti-DNA Ab
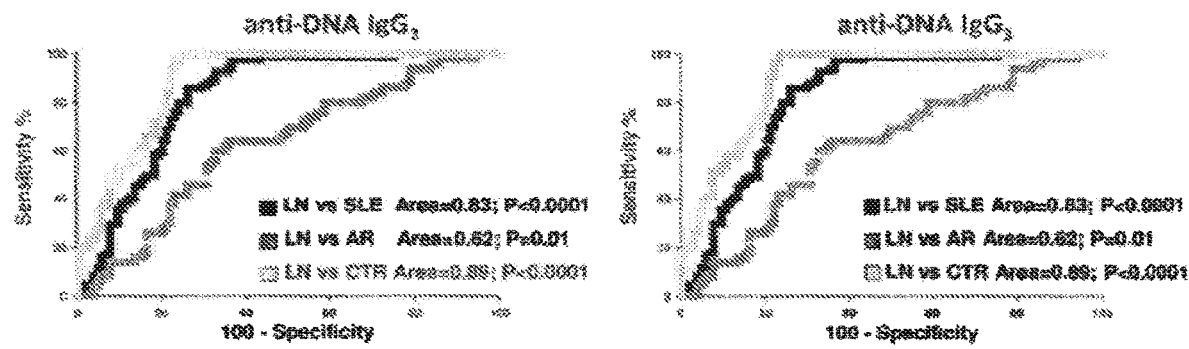

FIG. 11B

| Pat. num. | SEX | age | year of biopsy | LN Class | SCreat (mg/dL) | UProt (g/24h) | C3 (mg/dL) | C4 (mg/dL) | ANA | Anti-DNA | STEROID | CYCLOPH | CYCLOSP | MMF | PLAQUENIL |
|---|---|---|---|---|---|---|---|---|---|---|---|---|---|---|---|
| 1- | M | 16 | 2010 | IV | 0.5 | 2.2 | 103 | 16 | pos | pos | si | no | no | no | no |
| 2- | M | 22 | 2008 | III | 0.6 | 0.9 | 44 | 8 | pos | pos | si | no | no | no | no |
| 3- | M | 19 | 2010 | V | 2.4 | 0.9 | 78 | 12 | pos | pos | si | no | no | no | no |
| 4- | F | 18 | 2009 | IV | 0.4 | 1.4 | 65 | 10 | pos | pos | si | no | no | no | no |
| 5- | F | 23 | 2005 | V | 0.5 | 1.1 | 47 | 19 | pos | pos | si | no | no | no | si |
| 6- | F | 28 | 2005 | nd | 2.1 | 0.2 | 102 | 20 | pos | pos | si | no | si | si | no |
| 7- | F | 30 | 2007 | II | 0.4 | 0.6 | 60 | 10 | pos | pos | si | no | no | no | no |
| 8- | F | 17 | 2009 | IV-V | 0.7 | 0.6 | 47 | 8 | pos | pos | si | no | no | no | si |
| 9- | F | 25 | 2004 | IV | 0.9 | 1.2 | 5 | 20 | pos | pos | si | no | no | no | si |
| 10- | F | 43 | 2010 | IV | 0.5 | 1.4 | 53 | 6 | pos | pos | si | no | no | si | si |
| 11- | F | 44 | 2010 | II+V | 0.7 | 0.9 | 46 | 4.5 | pos | pos | si | no | no | si | si |
| 12- | F | 53 | 2010 | III | 0.6 | 2.3 | 141 | 18 | pos | pos | si | no | no | si | no |
| 13- | F | 34 | 2009 | IV | 0.9 | 2.6 | 53 | 11.5 | pos | pos | si | si | no | no | si |
| 14- | F | 48 | 2009 | III | 0.5 | 1.4 | 71 | 10.7 | pos | pos | si | no | no | si | si |
| 15- | F | 25 | 2009 | V | 0.6 | 3.3 | 63 | 13.1 | pos | pos | si | no | no | si | si |
| 16- | F | 29 | 2009 | IV | 0.6 | 4.5 | 41 | 4.1 | pos | pos | si | si | no | no | si |
| 17- | F | 30 | 2009 | IV | 1.0 | 1.9 | 75 | 10 | pos | pos | si | no | no | si | si |
| 18- | F | 35 | 2010 | IV | 0.7 | 2.1 | 47 | 2.5 | pos | pos | si | si | no | no | si |
| 19- | F | 31 | 2011 | IV | 0.8 | 5.7 | 23 | 2.4 | pos | pos | si | no | no | si | no |
| 20- | F | 27 | 2011 | nd | 1.0 | 1.0 | 50 | 5 | pos | pos | si | no | no | no | no |

FIG. 11C

| spot | Gene | Protein | Technique | score | coverage |
|---|---|---|---|---|---|
| A | TBA1B | alpha-1B Tubulin (chain) | MALDI-MS | 1011 | 48.8 |
|   | TBB5 | beta 2 Tubulin (chain) |  | 961 | 42.6 |
| B | GSHB | Glutathione synthetase | MALDI-MS | 712 | 32.7 |
| C | HSP7C | 'Heat shock cognate' 71 kDa | MALDI-MS | 1087 | 36.1 |
| D | PEPD | Xaa-Pro dipeptidase | MALDI-MS | 208 | 13.4 |
| E | EZRI | Ezrina | MALDI-MS | 679 | 23.7 |
|   | MOES | Moesina |  | 1465 | 45.8 |
| F | TKT | Transketolase | MALDI-MS | 713 | 27.4 |
| G | ANXA1 | Annexin A1 | MALDI-MS | 1575 | 74.3 |
| H | LDHA | L-lactate dehydrogenase a (chain) | MALDI-MS | 507 | 32.8 |
| K | VIM | Vimentin | MALDI-MS | 512.3 | 57.5 |
| J | HSPB1 | 'Heat shock' proteina beta-1 | MALDI-MS | 521 | 41.5 |
|   | PRDX6 | Peroxiredoxin-6 | MALDI-MS | 838 | 63.8 |
| I.1 | ENOA | Alpha enolase | LC-MS | 94.3 | 13.9 |
| I.2 | ENOA | Alpha enolase | LC-MS | 178.4 | 18.2 |
| I.3 | ENOA | Alpha enolase | LC-MS | 194.3 | 18.8 |
| I.4 | ENOA | Alpha enolase | LC-MS | 99.2 | 14.2 |
| L | CNDP2 | Cytosolic non-specific dipeptidase | MALDI-MS | 279 | 19.4 |

FIG. 11D

|  | LN (n = 104) | SLE (n = 112) |
|---|---|---|
| Male sex | 11 (12%) | 17 (15%) |
| age (years) | 34 (14 – 77) | 47 (16 – 79) |
| Age at the beginning (years) | 26 (12 – 77) | 37 (7 - 79) |
| Disease duration (years) | 3 (0.1 – 24) | 7 (0 – 34) |
| Creatinine serum (mg/dl) | 0.9 (0.3 – 6.4) | 0.7 (0.5 – 1.7) |
| C3 (mg/dl) | 63 (24 – 147) | 87 (42 – 154) |
| Anti-DNA ratio | 2.9 (0 – 26.7) | 0.8 (0 – 11.8) |
| Anti-C1q (U/ml) | 166 (10 – 600) | 21 (10 – 257) |
| Proteinuria (g/day) | 2.5 (0.1 – 20) | 0.1 (0 – 0.3) |
| Therapy |  |  |
| None | 19 (20%) | 30 (27%) |
| Steroids | 39 (42%) | 20 (18%) |
| Multiple therapies | 35 (38%) | 62 (55%) |
| LN class |  |  |
| Proliferative | 52 (56%) |  |
| Membranous | 11 (12%) |  |
| Mixed | 30 (32%) |  |

IN VITRO METHOD FOR PREDICTING, DIAGNOSING AND MONITORING IN THERAPEUTIC FOLLOW UP LUPUS NEPHRITIS

This is the U.S. national phase under 35 U.S.C. 371 of International Application No. PCT/IB2015/050388, filed 19 Jan. 2015, which designated the U.S. and claims priority to Italian Patent Application No. RM2014A000027, filed 20 Jan. 2014; the entire contents of each of which are hereby incorporated by reference.

TECHNICAL FIELD OF THE INVENTION

The present invention relates to the characterization of nephrotoxic antibodies in patients with lupus nephritis. On such nosologic evolution an in vitro method for the prediction, the diagnose of lupus nephritis in subjects affected or potentially affected by systemic lupus erythematosus, an in vitro method for monitoring a therapy against lupus nephritis in subjects affected or potentially affected by systemic lupus erythematosus and a kit for predicting the progression of lupus nephritis and/or for monitoring a therapy against lupus nephritis in subjects suffering or potentially suffering from lupus erythematosus are proposed.

STATE OF PRIOR ART

Lupus nephritis (LN) is a clinical-pathological condition characterized by an alteration of the renal structure and function which can affect subjects suffering from systemic lupus erythematosus (SLE). In particular, a relevant percentage of patients affected by SLE develops such condition which, if not recognized and treated in time, can lead to renal insufficiency and death. On the contrary, a quick diagnose of lupus nephritis, and if possible its prediction, opens to the use of effective and potentially resolving drugs if used upon the disease's beginning.

Different scientific proofs show that LN is mediated by the deposition of antibodies in the glomeruli.

Among the theories proposed by scientists about the development of LN, the prevailing one suggests that anti-dsDNA circulating antibodies (double strand DNA) or antibodies versus proteic components of DNA, such as histones, can cross-react with glomerular constituents by forming sub-epithelial and mesangial immuno-deposits. In particular, it was assumed that chromatin and histones contribute to act as trigger for the deposition of other antibodies not facing DNA as, due to the positive charge thereof, the combination of chromatin and histones links to negatively loaded components of the glomerular basal membrane, especially heparin sulphate and proteoglycans, by becoming target antigens for other antibodies facing proteic structures of the renal glomerulus (podocytes and basal membrane).

Nowadays this theory does not clarify the mechanisms leading to the formation of the immune deposits and the consequent occurrence of renal lesions in subjects with SLE. In particular, it is not clear which is the general role of the triggering antibodies (i.e. anti-DNA) and if they act as trigger or take part in the antibody deposit mechanism. More generally, the fact that high-level silk anti-Dna antibodies are present in almost all patients with SLE, but only a portion thereof develops the renal disease, indicates that concomitant and probably majority factors have a central role in determining renal lesions. As LN is characterized by deposit in the glomeruli of auto-antibodies, a mechanism linked to the formation of anti-kidney antibodies and more precisely directed towards cellular components of the renal glomerulus, such as the podocyte cells, can be assumed. It is clear that there is the need for verifying directly in the lesion seat, that is in the renal glomerulus, the composition of the auto-antibodies and that only after having clarified this item one can proceed with identifying early disease markers. The absence of an effective marker for lupus nephritis translates into the impossibility for the clinician to identify early the patients who will develop LN and adopt the most suitable therapeutic approach. Still nowadays diagnostics is based upon the evaluation of aspecific circulating antibodies (ANA, antiDNA, antiC1q) which can be involved in the disease pathogenesis, but which, indeed as circulating, could not have specificity for the kidney and only generically associated to the development of renal lesions.

The need for identifying specific markers of lupus nephritis in man and developing not invasive diagnostic/prognostic instruments allowing a possibly early diagnosis of lupus nephritis in subjects affected by systemic lupus erythematosus is shared by the scientific community in order to define a suitable and timely therapeutic strategy. The use thereof in the therapeutic follow up would provide a crucial help to the clinician in the attempt of modulating a therapy which usually is long and provides several therapeutic associations involving drugs with high toxicity.

SUMMARY OF THE INVENTION

The present invention relates to an in vitro method based upon determining circulating antibodies able to predict, diagnose and monitor lupus nephritis (LN) in the therapeutic follow up in subjects affected by systemic lupus erythematosus (SLE) and it provides the use of specific antibodies versus endogenous or planted renal antigens representing the target of the antibody damage in lupus nephritis. The search starting objective which brought to the discovery was the characterization of the target antigens existing in the kidney, seat of the inflammatory lesion, that is of the glomerular nephritis. Based upon the results of the renal study which brought to the identification of specific auto-antibodies versus endogenous and planted herein proteins, then one reached the determination of the same antibodies in the serum and the demonstration that high circulating levels are associated to the presence of LN. Such research was carried out for the first time on man by using renal tissue directly obtained by means of in vivo organ biopsy. The conclusions deriving therefrom then are based upon studies which for the first time were carried out on human renal tissue and made possible by the development of the proteomic survey techniques (laser capture, mass spectrometries, two-dimensional electrophoresis, etc.).

The present invention is based upon the finding that subjects affected by systemic lupus erythematosus, and wherein alterations of the renal structure and function typical of lupus nephritis are observed, have higher renal and circulating levels than some autoantibodies of the IgG2 isotype, antibodies having as antigenic target endogenous proteins expressed by the kidney such as α-enolase, Annexin AI and/or proteins herein planted such as DNA, and several classes of histones (histone 2a, 3, 4). The demonstration of the presence in the renal glomerulus of antibodies of IgG2 class versus the above proteins (that is α-enolase, Annexin AI and the several classes of histones), carried out for the first time by the inventors of the present invention, represents the basis of the herein-described invention. The identification of new target proteins of nephrotoxic (above all anti-αenolase) antibodies and the characterization of the specific IgG2 isotype of the antibodies for lupus nephritis allow evolutions both on the mechanisms involved in the renal damage and on the possibility of evaluating directly the renal and circulating of such specific antibodies as disease markers. In fact, herein it is demonstrated that patients affected by lupus nephritis have high concentrations of anti-αenolase and anti-annexin AI, anti-histones of class 2a, 3 and 4 IgG2 with respect to the controls made by patients not having lupus nephritis. The novelty of the prevailing IgG2 isotype is herein reported even for the antibodies versus DNA. Then, it is important noting that there is a multiple composition of the autoantibodies involved in LN but it is herein demonstrated that such promiscuity is very selective and it has as target only some endogenous renal proteins and/or antigens planted therein and furthermore it involves in specific way antibodies of IgG2 isotype. As demonstrated in the herebelow section "Materials and Methods", higher levels of IgG2 versus the anti-αenolase and anti-annexin AI antigens, anti-histones of class 2a, 3 and 4 in patients who develop or will develop LN are demonstrated with respect both to healthy subjects, and subjects affected by SLE without nephritis or subjects affected by nephritis with different aetiology from the systemic lupus erythematosus.

It is to be noted that the concomitant presence in the serum of antibodies of IgG2 isotype with respect to the panel of antigens detected in the renal tissue (that is α-enolase, annexin AI, histone 3 and DNA) identifies patients with SLE with high specificity and sensibility (area below the curve in ROC >0.85; P<0.001) and with respect to other rheumatological diseases (for example Rheumatoid Arthritis) and normal people.

In particular, anti-αenolase, anti-annexinA1 IgG2 antibodies and anti-histone 2A, 3 and 4 IgG2 can be advantageously used as markers of lupus nephritis. In fact, the use thereof as markers has demonstrated a highly sensible and specific instrument for the nephritis associated to systemic lupus erythematosus since they result absent in samples of subjects affected by nephritis with different aetiology from SLE and they do not cross-react with other potential renal antigens.

It appears clear that one of the advantages associated to the herein-described invention consists in the possibility of obtaining a diagnosis of LN with significative advance with respect to the beginning of the typical symptoms of this pathology such as, for example, an important renal deficit.

A particularly advantageous aspect of the present invention is that anti-αenolase, anti-annexinAI, anti-histone2A, 3 and 4 IgG2 antibodies can be dosed even in a blood or serum sample without the need then of intervening in invasive way on the subject by means of a renal tissue collection by biopsy.

Therefore, it is herein described for the first time a specific, sensible and a little invasive in vitro method for predicting, diagnosing and/or monitoring in therapeutic follow up lupus nephritis in subjects affected by systemic lupus erythematosus.

Therefore a first subject of the present application is formed by:
an in vitro method for predicting, diagnosing and monitoring in therapeutic follow up lupus nephritis in a subject affected or potentially affected by systemic lupus erythematosus comprising the following steps:
a) determining the concentration of IgG2 antibodies versus at least one of the antigens selected from the group: αenolase, annexin AI, histone 2A, histone 3, histone 4 and DNA in a biological sample of said subject;
b) comparing said concentration in said biological sample with a control value
wherein an increase in the concentration of said antibodies with respect to said control value indicates a development of lupus nephritis.

A second subject of the present invention is:
an in vitro method for monitoring the progression of lupus nephritis in a subject affected by systemic lupus erythematosus comprising the following steps:
a) determining the concentration of IgG2 antibodies versus at least one of the antigens selected from the group: αenolase, annexin AI, histone 2A, histone 3, histone 4 and DNA in at least a first and in at least a second biological sample of said subject, said at least a first and a second sample obtained at different times,
b) comparing said concentration obtained for said at least first and second sample.

It is also a subject of the present invention a kit for predicting and/or diagnosing lupus nephritis and/or for monitoring a therapy against lupus nephritis in subjects suffering or potentially suffering from lupus erythematosus comprising:
at least an aliquot of one or more reagents for the determination of IgG2 antibodies versus at least one of the antigens selected from the group: αenolase, annexin AI, histone 2A, histone 3, histone 4 and DNA in a biological sample of said subject and
at least an aliquot of one positive control comprising IgG2 versus at least one of the antigens selected from the group: αenolase, annexin AI, histone 2A, histone 3, histone 4 and DNA. An additional subject of the present invention is an in vitro method for diagnosing the presence of SLE and LN in a given subject and differentiating them from other rheumatological conditions and from other primary glomerulonephritises. In particular the method comprises the following steps:
a) determining the levels of auto-antibodies of IgG2 isotype versus all target antigens from the group: αenolase, annexin AI, histone 3 and DNA in a biological sample of said subject and
b) comparing the levels of the above auto-antibodies with those obtained starting form a control sample,
wherein an increase in the levels of said auto-antibodies with respect to said control levels indicates the presence of SLE and LN in the subject.

Additional advantages, as well as the features and the use modes of the present invention will result evident from the following detailed description of some preferred embodiments, shown by purely way of example and not with limitative purpose.

DESCRIPTION OF THE FIGURES

FIGS. 1 *a-d* show the presence in the glomerular eluates of patients with LN antibodies versus some renal antigens which are marked with alphabet capital letters from A to L; their identification is shown explicitly in table 2. FIGS. 1 *e-f* show the presence in serum of some of the antibodies detected in the kidney of the same patients (FIG. 1*a*) with LN.

representing graphically as colour scale (heat intensity map) the hierarchical analysis for families of antibodies, all belonging to IgG2 class against all antigens.

Figure 2A:
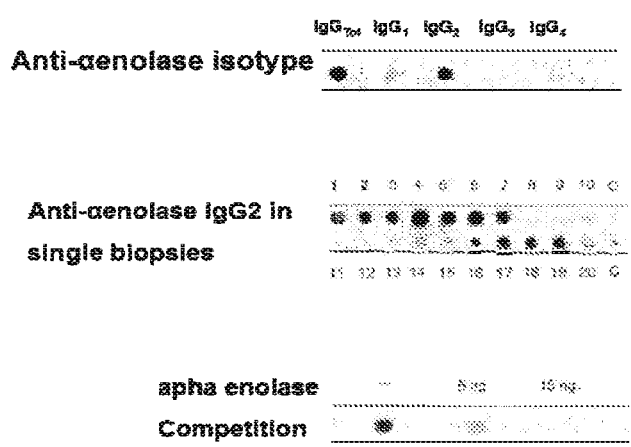
FIGS. 2 *a-e* show the expression in the single biopsies of patients with LN and the possible isotypes, respectively of the antibodies anti-α enolase (FIG. 2*a*), anti-annexin AI (FIG. 2*b*), anti-histone H1, H2A, H2B, H3, H4 (FIG. 2*c*), anti-DNA (FIG. 2*d*), anti-C1Q (FIG. 2*e*) in glomerular eluates of patients. The concomitance of positivity of the single antibodies in the single biopsies is shown in (f)
Figure 2B:
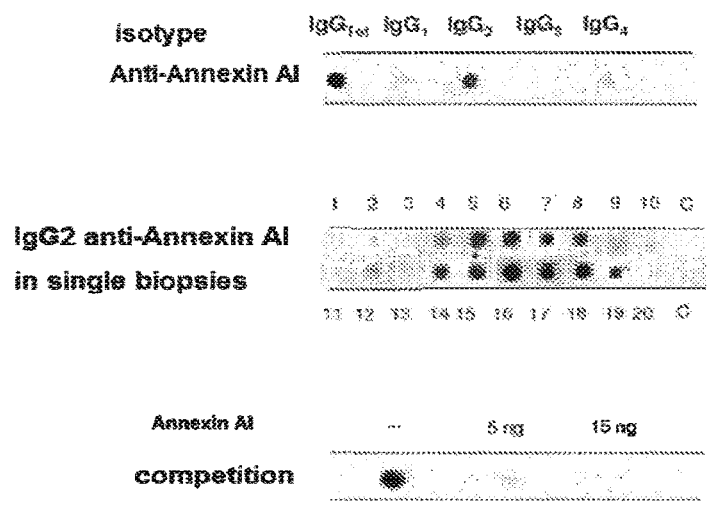
Figure 2C:
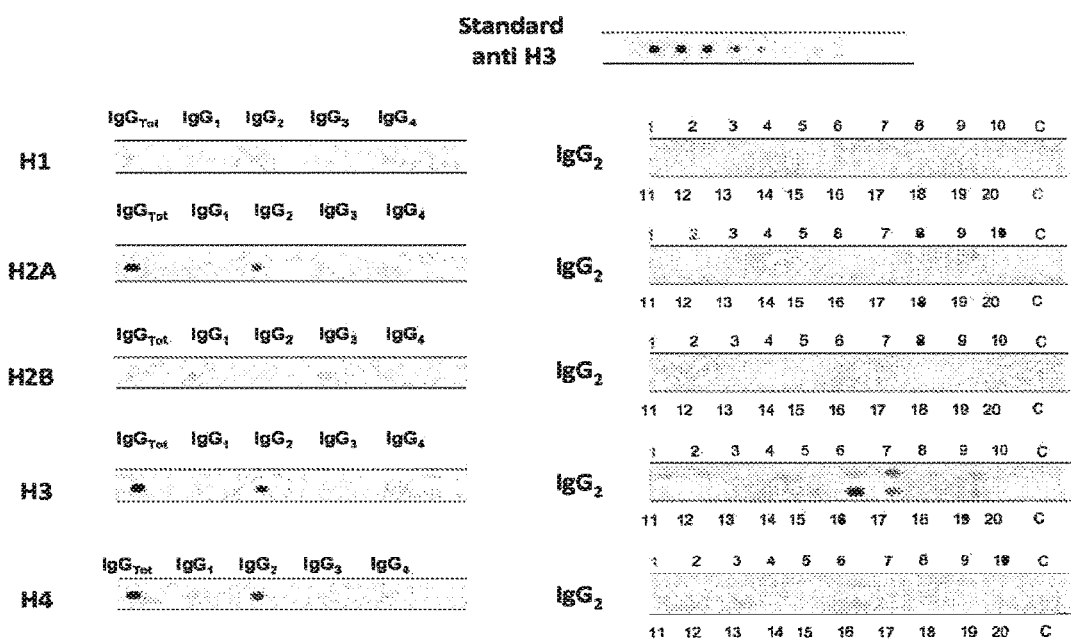
Figure 2D:
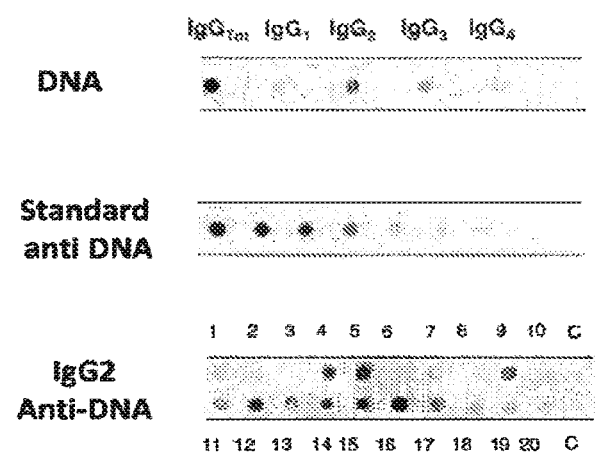
Figure 2E:
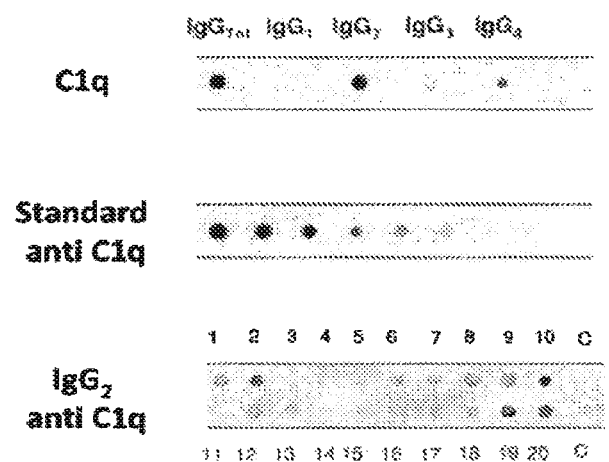
Figure 2F:
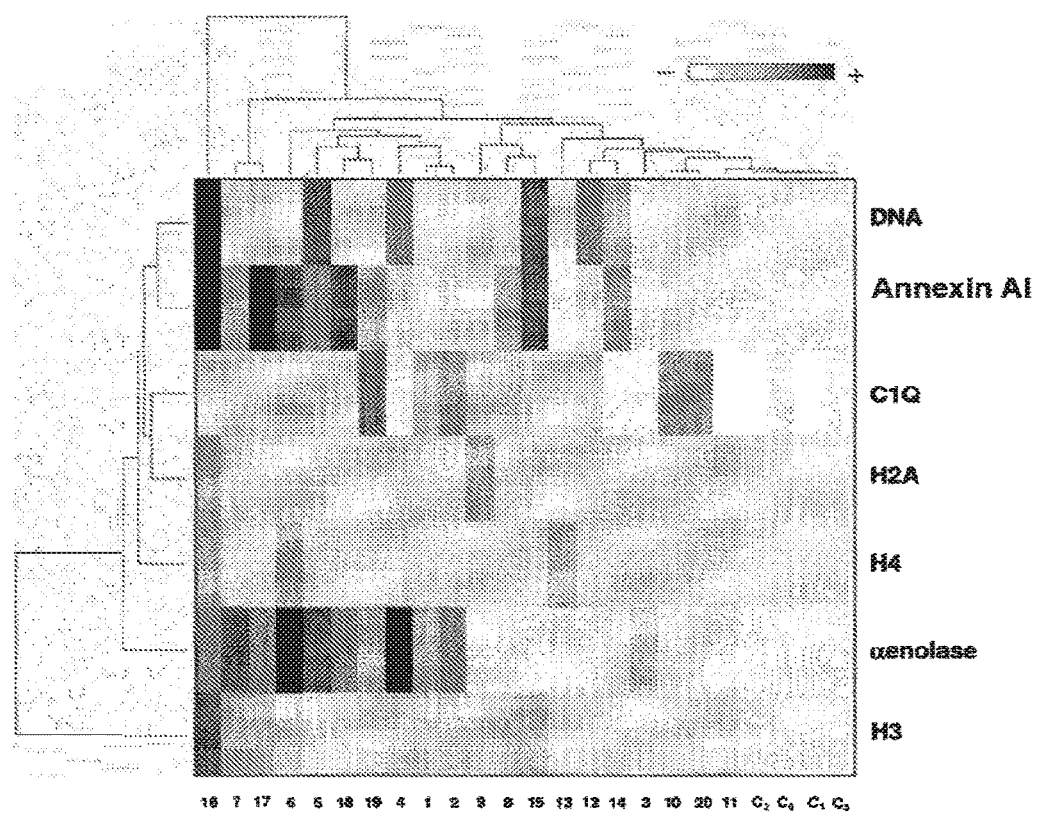
Figure 3A:
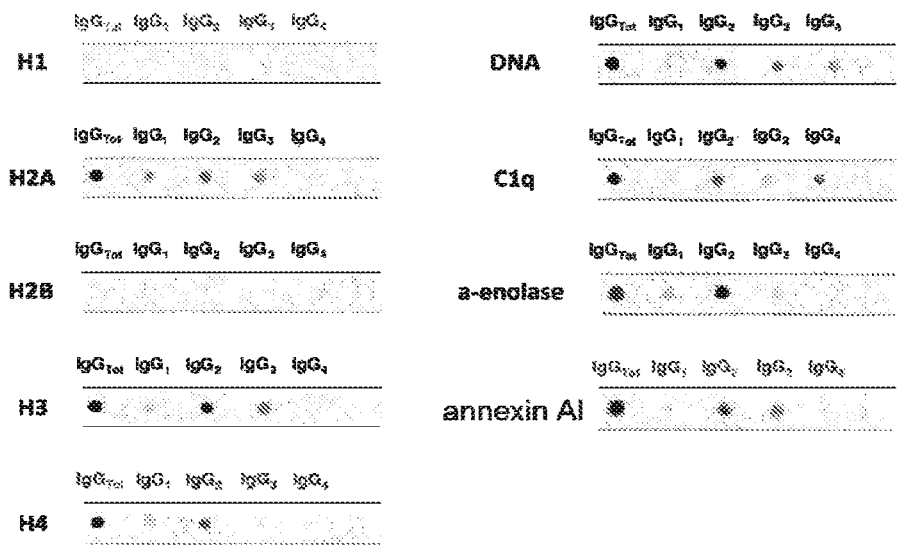
Figure 3B:
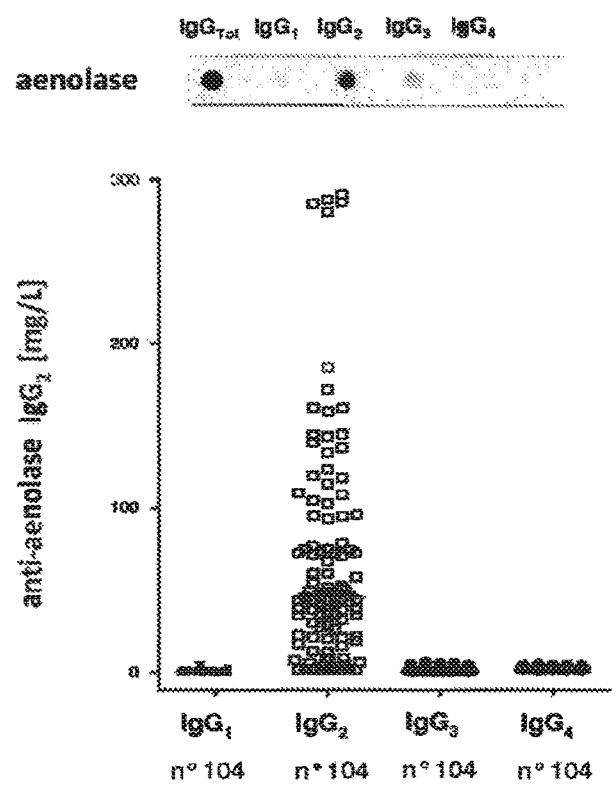
Figure 3C:
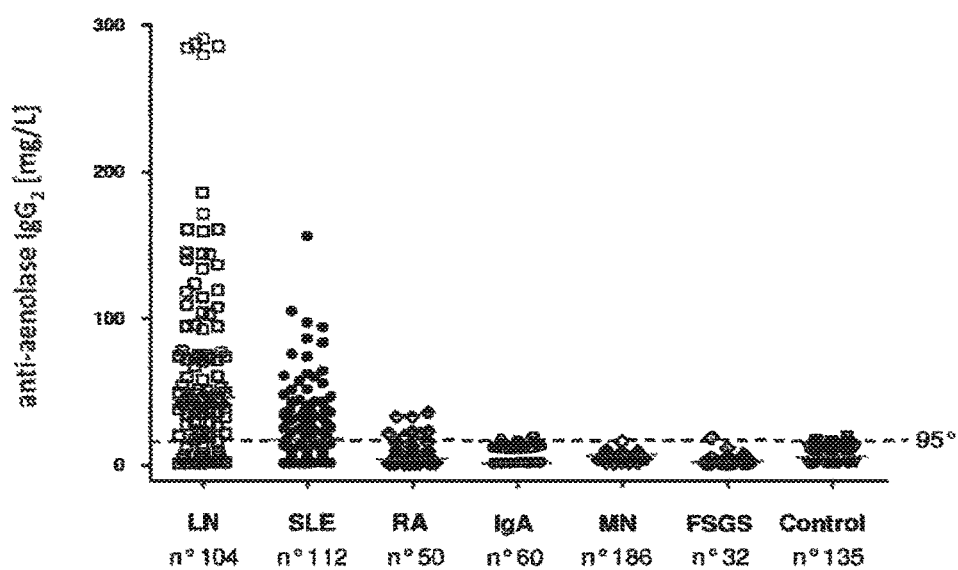
Figure 3D:
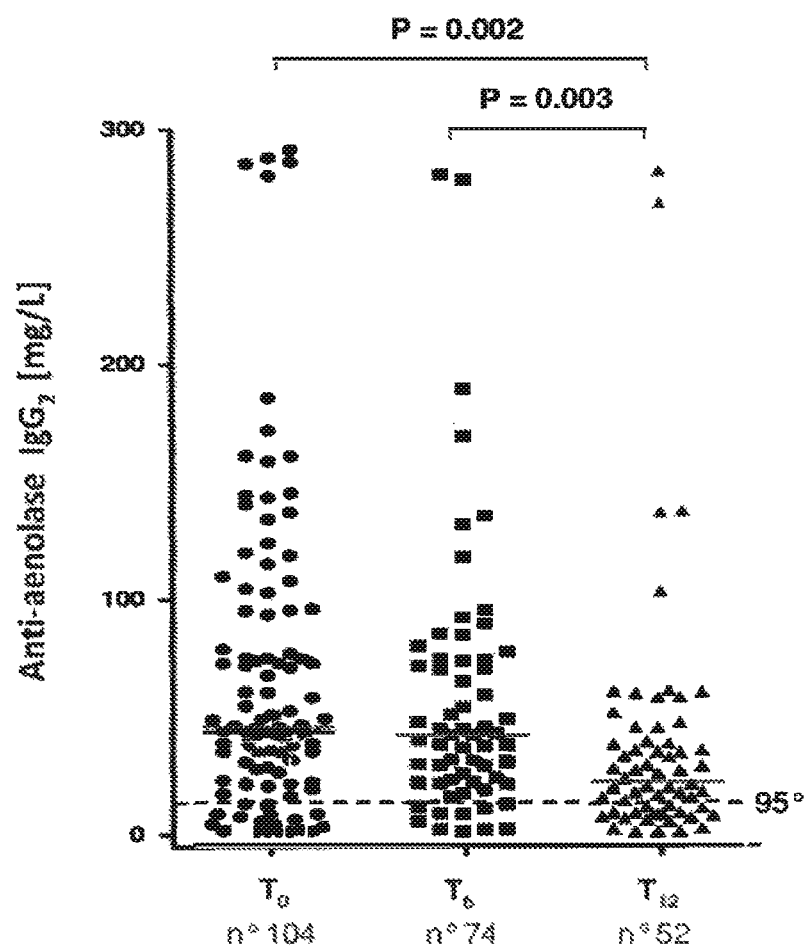

FIG. 3a shows a dot blot relative to the characterization of all prevailing isotypes in serum of antibodies versus the different classes of antigens of the invention. It derives that in serum there is a lesser specificity of the antibodies as it can be demonstrated in addition to IgG2 (which remains the main isotype) antibodies even of IgG1 and IgG3 isotype. FIG. 3b shows the data related to the serum levels of all anti-αenolase isotypes. FIG. 3c shows the levels of anti αenolase IgG2, in patients with flourishing LN, SLE, RA (rheumatoid arthritis) and/or with other idiopathic nephritis (membranous nephritis—MN, focal segmental glomerulosclerosis-FSGS, nephropathies with deposits of IgA-IgA) with respect to patients with SLE and the fact that such values decrease during the phase of immunosuppressive therapy that is after 6 months (T6) and 12 months (T12) as from the beginning of specific immunodepressive therapies (figure c and figure d).

Figure 4C:
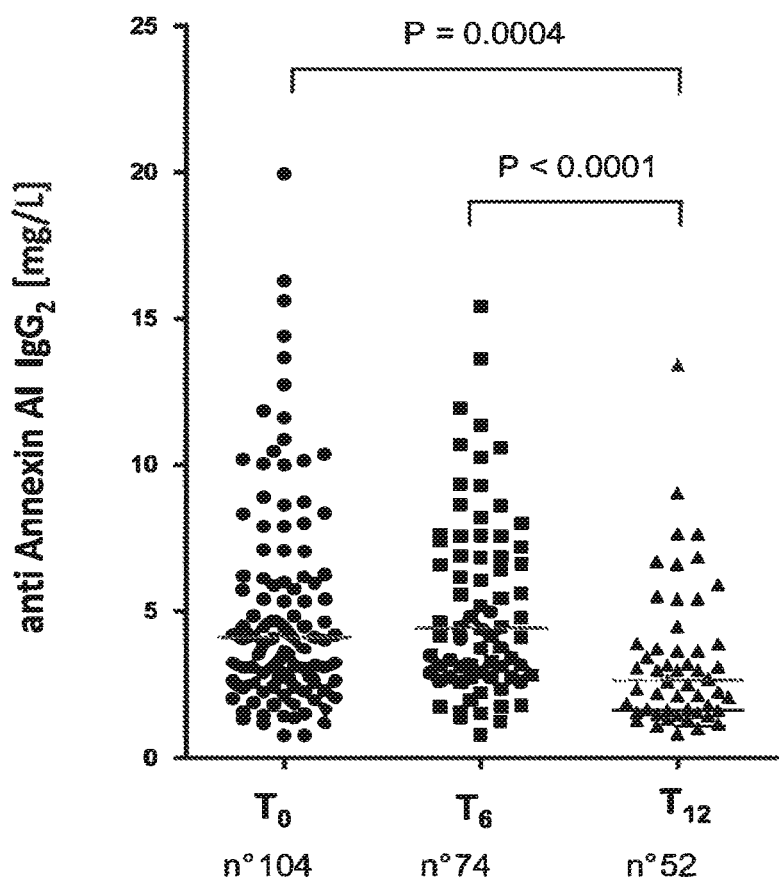

FIG. 4 shows the isotype of the serum antibodies anti-annexin AI (a) and the circulating levels of anti-annexin AI IgG2 (b) in patients with flourishing LN and/or with SLE but without nephritis and in other classes of patients with rheumatoid arthritis (RA) and with other nephritis (MN, IgA, FSGS). In (c) the levels of the same antibodies before (T0) and after 6-12 months of immunodepressive therapy (T6 and T12) are shown.

Figure 5A:
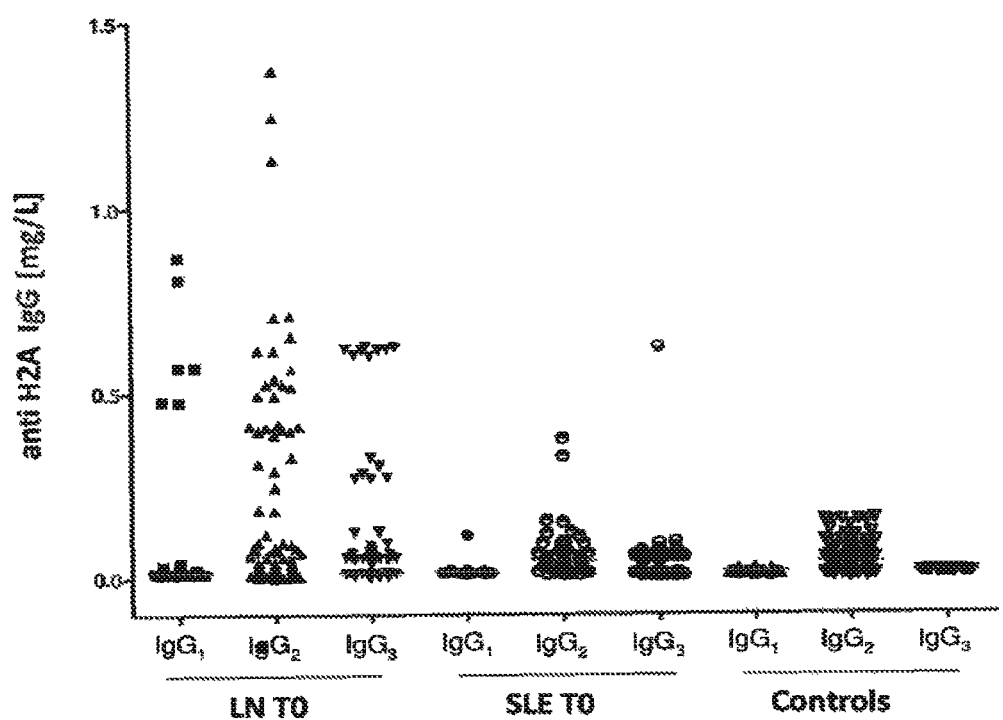
Figure 5B:
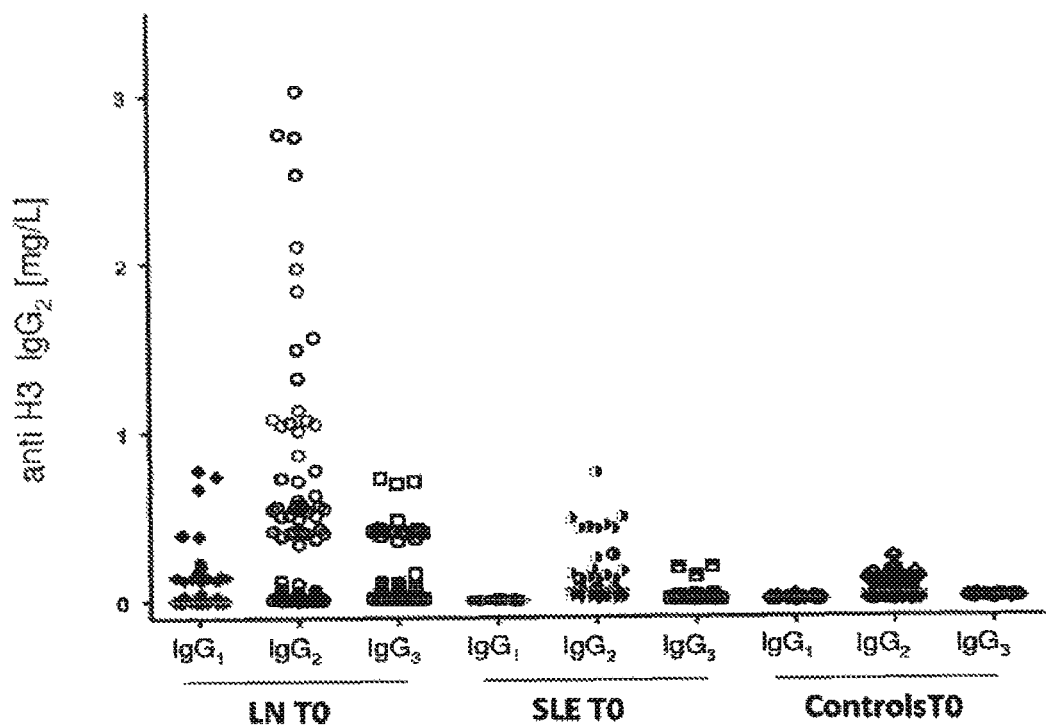
Figure 5C:
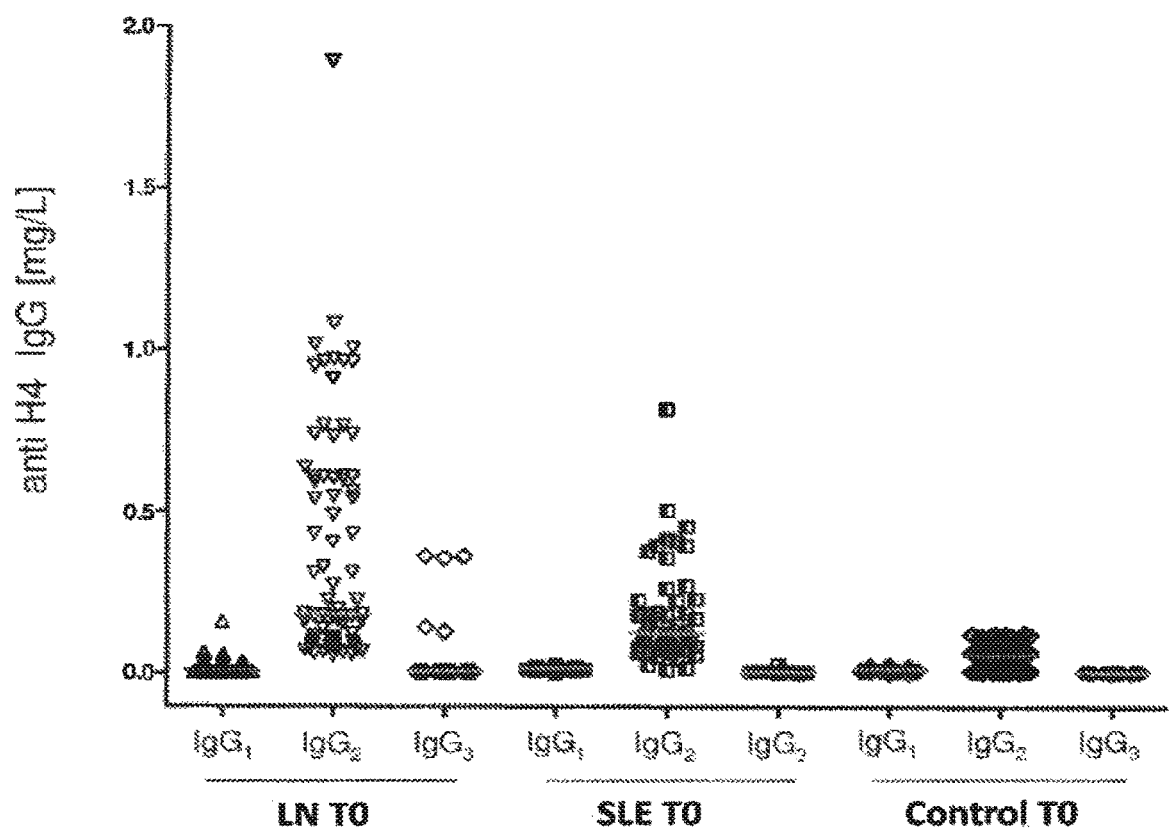

FIG. 5 shows the serum levels of antibodies anti-histone 2A, 3 and 4 (respectively FIG. 5a, 5b, 5c) in patients with LN and SLE.

FIGS. 6 a-c show the specificity of antibodies anti-αenolase of IgG2 isotype evaluated by comparing the reactivity of antibodies of IgG2 isotype purified by serum of patients with LN (structures shown in FIG. 6b) with the reactivity of antibodies anti-αenolase of IgG4 isotype purified by patients with membranous nephritis (structure shown in FIG. 6c). The specificity was evaluated by using fragments of αenolase obtained with CNBr (a). The results showed that IgG2 and IgG4 recognized different peptides derived from CNBr fragmentation, that is respectively the products with 1.3 KDa and 6.8 kDa.

(d) Evaluation of homologies between human lupus nephritis and that of the mouse. The herein studied LN murine model is that with spontaneous lupus (MRL-Ipr/Ipr) activating cell clones (IgG2 clone H147) inducing nephritis in mouse. The target antigen of antibodies deriving from this cell clone ((IgG2 clone H147) was recognized to be as a protein of 46 kDa which herein is demonstrated to be αenolase.

Figure 7:
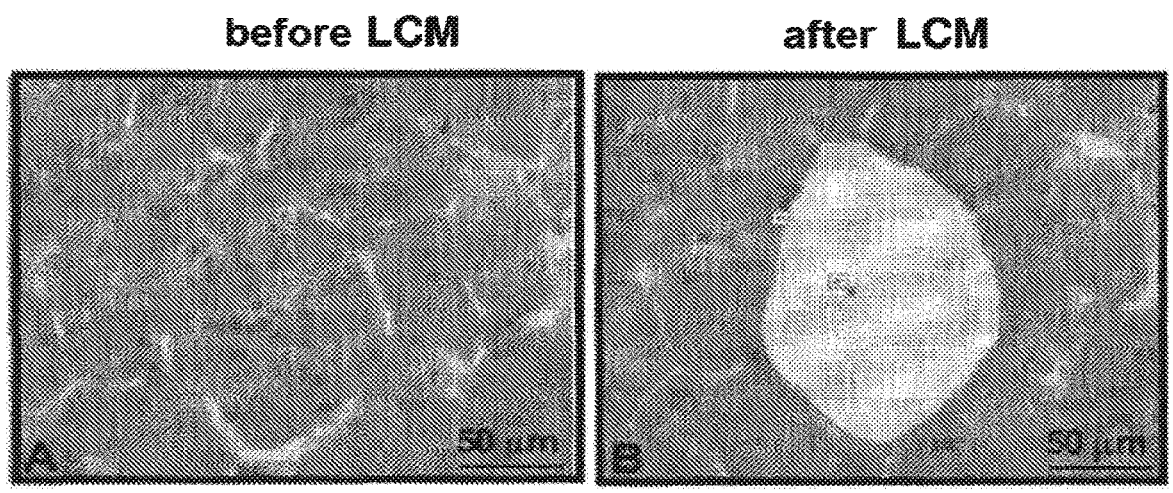

FIG. 7 shows: a) renal fragment before the micro-dissection by means of 'laser-capture', b) result of the micro-dissection by means of 'laser capture'. This figure shows that only the glomerular cells were removed from the laser micro-dissection by showing that the auto-antibodies deriving from the micro-sectioned tissue have clearly glomerular origin.

Figure 8:
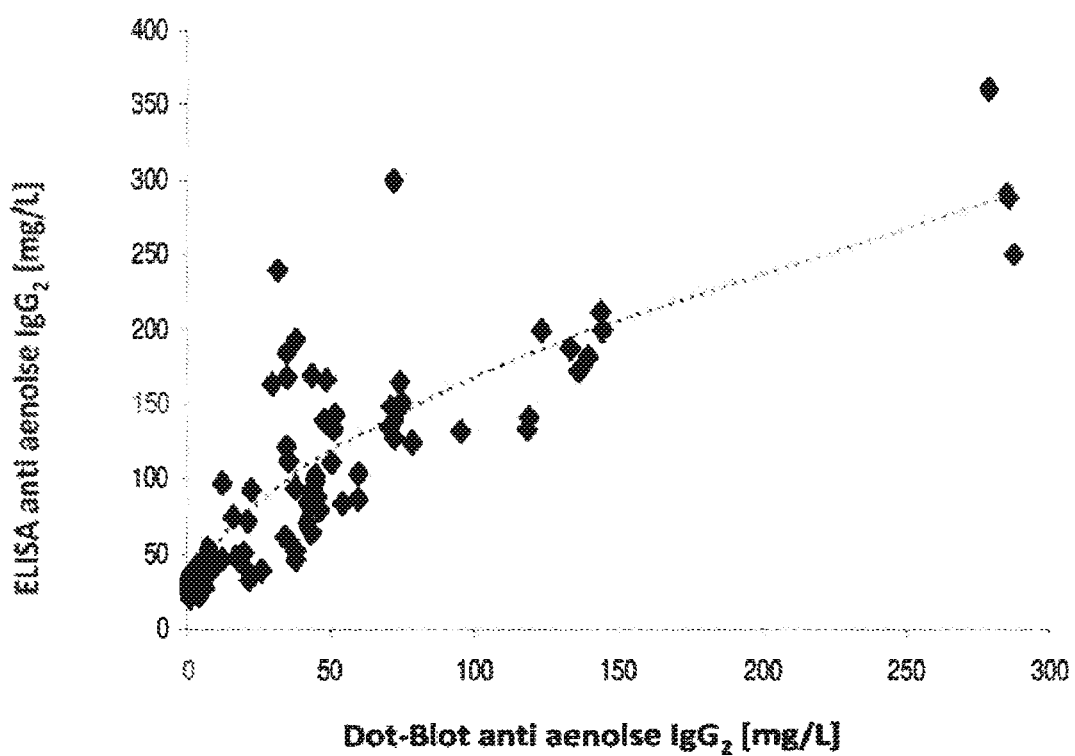

FIG. 8 shows the correlation of the circulating levels of anti-αenolase IgG2 determined with two different methods (ELISA and dot-blot).

Figure 9A:
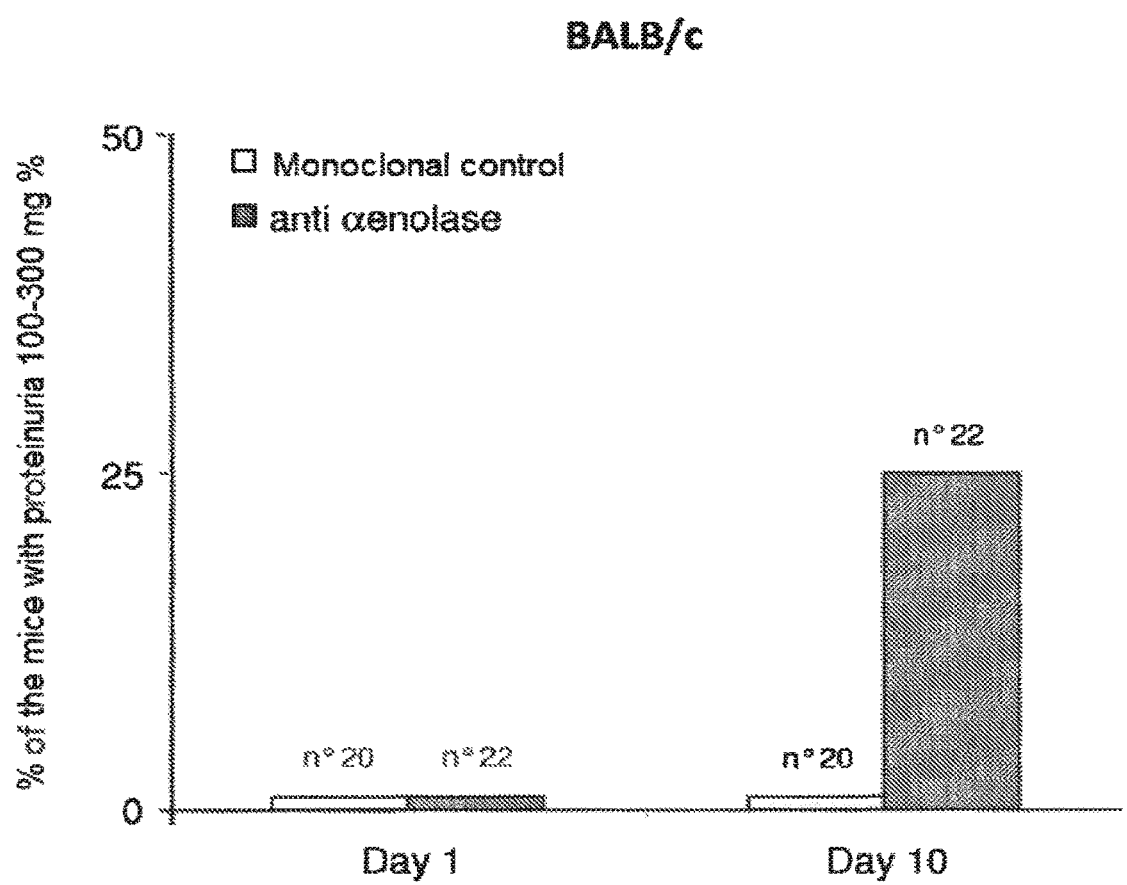
Figure 9B:
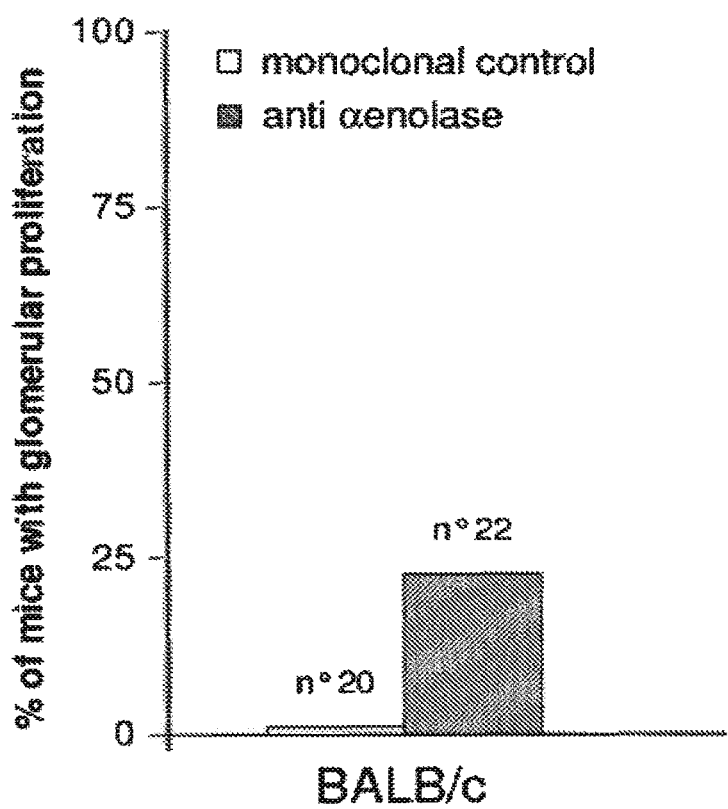

FIG. 9 shows: a) a graph related to the percentage of BALB/c mice with proteinuria after intra-peritoneal injections with hybridoma producing IgG anti-αenolase antibodies or IgM anti-dsDNA antibodies as negative control; b) the percentage of BALB/c mice with proliferative glomerular lesions after intra-peritoneal injections with hybridoma producing IgG anti-αenolase antibodies or IgM anti-dsDNA antibodies as negative control.

FIG. 10

Figure 10A:
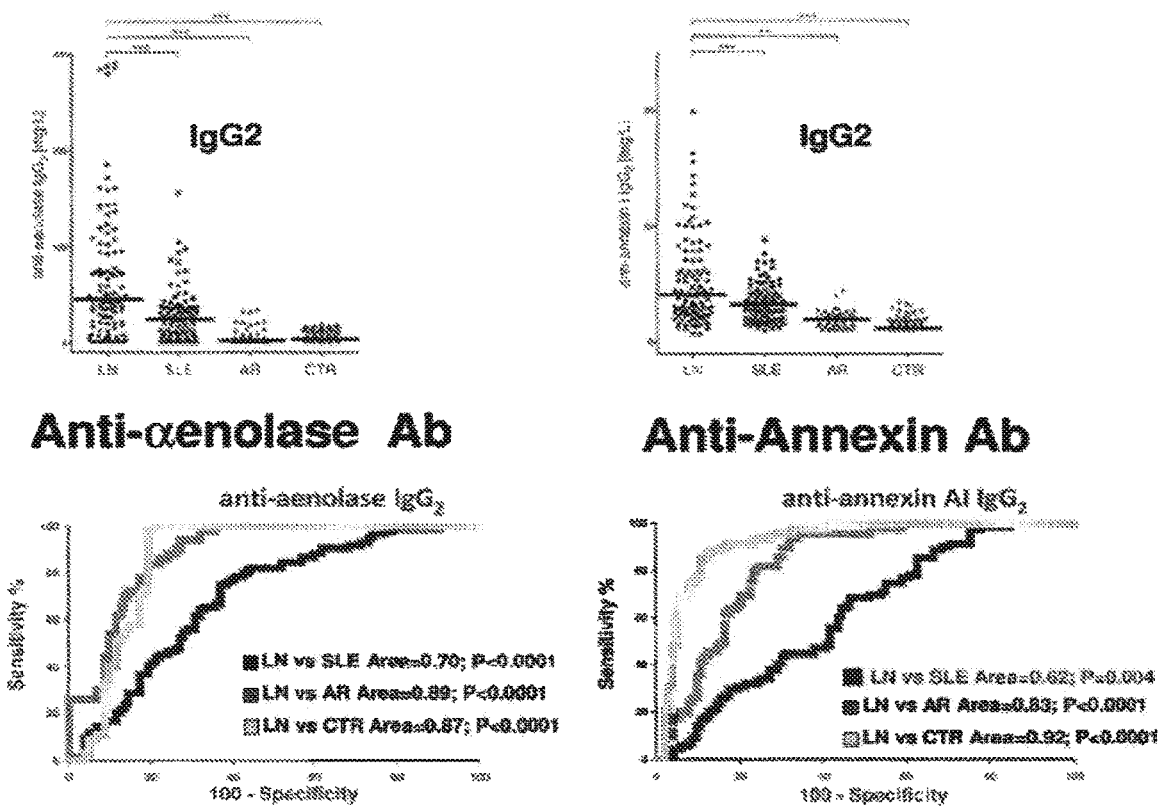

FIGS. 10A-C show after defining the isotypes related to all glomerular autoantibodies, the serum levels of the most relevant isotype were determined by means of ELISA in 184 patients with LES, 104 thereof had LN. The results are expressed as median inter-quartile range. ROC Curves were calculated for the antibodies with high circulating levels for determining the specificity and the sensibility with respect to SLE, rheumatoid arthritis and normal subjects. (a) anti-αenolase and IgG2 anti-annexin AI IgG2; (b) anti-H3 IgG2 and IgG3; (c) anti-DNA IgG2 and IgG3.

FIG. 11A

Figure 11A:
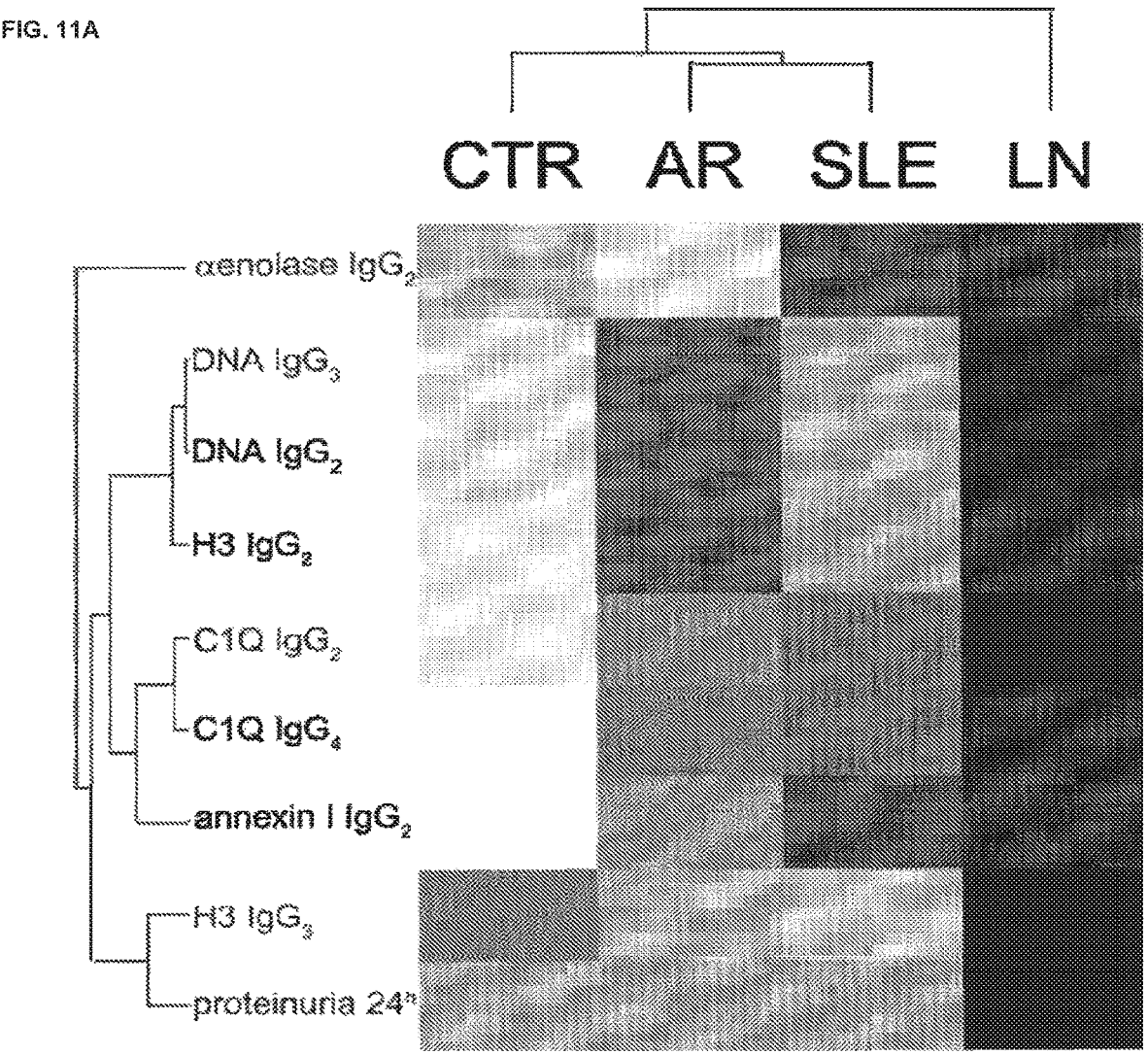

FIG. 11A shows the serum levels of each relevant autoantibody were analysed with Hierarchical Cluster Analysis (HCA) which joins and compares contemporarily the serum levels of each specific antibody (and comprises different isotypes); the resulting heat map wherein colours from (maximum) dark to (minimum) white designate the related abundances, it gives and evaluation of how the different parameters identify different groups of patients. It seems that serum anti-αenolase and anti-annexin AI IgG2 separate LN and AR better than other antibodies whereas anti-H3, and anti-DNA IgG2/IgG3 allow distinguishing LN from SLE.

FIG. 11B

FIG. 11B shows the clinical features related to the 20 patients with lupus nephritis who had a renal biopsy diagnosing the disease and who were studied for the presence of antibodies deposited in the kidney versus renal proteins. All patients had clinical signs from glomerulo nephritis and humoral of lupus erythematosus.

Abbreviations: LN, Lupus nephritis; SCreat, creatinine in serum; UProt, proteinuria; ANA, antinuclear antibodies.

FIG. 11C

FIG. 11C shows the spectra obtained with MALDI-MS/LC-MS and related to the proteic spots (A-L) by 2D electrophoresis as shown in FIG. 1. The proteins identified with 2D-electrophoresis were characterized with MALDI (spot A, B, C, D, E, F, F, G, H, K, J, L) and/or with LC-MS (spot I); their identification is shown in the FIG.

Abbreviations: MALDI-MS=Mass spectrometry with Assisted Laser Matrix, LC-MS =Mass spectrometry with Liquid Chromatography—

FIG. 11D

FIG. 11D shows the clinical features of all patients enrolled in the study including patients with lupus erythematosus and lupus nephritis. The clinical features were defined upon collecting serum samples.

DETAILED DESCRIPTION OF THE INVENTION

The present invention relates to an in vitro method for predicting and/or diagnosing lupus nephritis (LN) in subjects affected by systemic lupus erythematosus (SLE), an in vitro method for monitoring a therapy against lupus nephritis in subjects affected by systemic lupus erythematosus and a kit for predicting the development of lupus nephritis and/or for monitoring a therapy against lupus nephritis in subjects affected by lupus erythematosus.

The method can even be used for a diagnosis of SLE in patients with clinical signs and with uncertain positivity to classical biomarkers of the disease and for the diagnose of LN in patients having urinary signs of active nephritis.

In Vitro Method for the Prediction and/or the Diagnose of Lupus Nephritis

The herein described in vitro method allows predicting and/or diagnosing lupus nephritis in a subject affected or potentially affected by systemic lupus erythematosus.

Under the expression "potentially affected" in the present invention a subject is meant therefor a diagnosis of systemic lupus erythematosus has been formulated, but not yet confirmed, based upon the general and (ANA, anti-DNA) humoral pathological symptoms and wherein the presence of renal lesions is not suspected or it is excluded momentarily. This involves that the positivity of auto-antibodies of IgG2 isotype with respect to one of the target antigens, as herein described, is more specific and sensible than the current criteria for diagnosing SLE.

Under systemic lupus erythematosus (herein designated even under the abbreviation SLE from the English term Systemic lupus erythematosus) in the present invention, according to what indicated in the medical/scientific literature, one relates to a chronical disease with autoimmune nature characterized by general clinical symptoms such as articular, neurological problems, development of cutaneous erythema, possible febrile attacks, inflammations to mucous membranes such as pleurae and pericardium. Such general symptoms often represent typical elements of the disease beginning which generally do not create particular problems of clinical management. However, the disease, can evolve by involving specific organs, such as the kidney, giving origin to a nephritis (thereof 6 classes are known defined by peculiar hystological aspects) which, if not treated, evolves towards the chronical renal insufficiency. The renal disease due to lupus is known as lupus nephritis and it can involve up to 50% of the patients affected by systemic lupus erythematosus. The occurrence of lupus nephritis is considered an important complication of the systemic lupus requiring targeted therapies with immuno-suppressors. If not timely identified and treated, generally it evolves towards the terminal chronical renal insufficiency so as to require dialysis and transplant. Furthermore, the disease is characterized by the presence of disease markers which by convention are considered specific of the same (Antinuclear antibodies, anti-DNA antibodies) but they give no information about the development of pathologies correlated to the target organs (see kidney) and do not provide any useful predicting data.

Under lupus nephritis, (herein designated even with the abbreviation LN from the English term Lupus nephritis) in the present invention, according to the clinical/medical practice, a clinico-pathology condition is meant characterized by an alteration of the structure and of the renal function during systemic lupus erythematosus that is a renal lesion having typical immunopathological features even in absence of lupus general markers. The pathological features are: a-the deposit in the renal glomeruli of antibodies versus immunoglobulins (IgG, IgA, IgM) as well as the complement (C3, C4, C1q); b—the presence of focal or diffused proliferative lesions (classes 1-4) and/or sub-epithelial deposits of immune complexes (class 5).

The in vitro methods described in the present invention aim at determining, preferably in the peripheral blood, antibodies which have been found in the kidney of the patients affected by LN and, therefore, herein characterized for the first time as the disease. The dosage thereof allows predicting and/or diagnosing LN early in subjects affected by SLE in absence or in presence even of slight symptoms which can be associated to lupus nephritis.

In particular, it is possible carrying out the diagnose not only in each one of the conventional stages (classes) of the disease, but even before the appearance of any clinical manifestation associated to LN. This will be crucial in order to follow the patients with lupus which have not yet developed renal signs, but wherein the future development of the lesions can be predicted by means of variations of the circulating levels of specific anti-αenolase, anti-annexinAI, ant-C1q, anti-histone2A, 3 and 4, DNA IgG2. Therefore, such method could be used in the follow up of patients with lupus already as from the beginning of the general clinical symptoms and in absence of renal involvement by preceding and providing the beginning thereof.

In particular, the herein described method characterizes in that it comprises a passage a) of determining the concentration of IgG2 antibodies of at least one of the antigens chosen from the group: αenolase, annexin AI, complement C1q, histone 2A, histone 3 and histone 4, DNA in a biological sample of a subject affected or potentially affected by systemic lupus erythematosus or thereof a generic diagnose of systemic lupus not complicated by organ pathology is known. In a preferred embodiment of the invention, the antibody thereof the concentration is determined is an anti-αenolase IgG2 antibody.

The determination of the concentration of the above antibodies starting from any biological material can be performed according to any one of the methods considered by the person skilled in the art suitable to this purpose. Such methods are widely known in literature and described in details in most part of the laboratory manuals, therefore it does not result to be necessary to examine them closely on this occasion.

By purely way of example, the concentration of the antibodies anti-αenolase, anti-annexin AI, anti-complement C1q, anti-histone 2A, anti-histone 3 and anti-histone 4 of IgG2 type, anti-DNA of IgG2 type in a biological sample can be determined by means of methods such as ELISA (enzyme-linked Immunoabsorbent assay), western-blot, RIA (radioimmunoassay), proteic arrays, dot-blot or mass spectrometry and in any case more generally with all techniques used in the clinical chemistry allowing to detect a reaction between an antigen and an antibody by detecting with quantitative methods the occurred reaction thereof. The above techniques exploit the possibility of making the antibody under evaluation to interact with the specific antigen and then to detect the quantity of antibody linked to specific antibodies versus the human IgG2; the last reaction is detected, for example, by means of horseradish peroxidase (HRP) conjugated to the anti-human IgG2 antibodies. The horseradish peroxidase, by catalysing the oxidation of a substrate thanks to the hydrogen peroxide, generates a coloured, fluorescent or luminescent product, which can be measured by means of spectrophotometer. It is obvious that any detecting system linked to the anti-IgG2 antibody can be used. In particular, the determining methods preferably will be immunological methods.

In an embodiment of the invention, the determination of the antibody anti αenolase, annexin AI, complement C1q, histone 2A, histone 3 and histone 4, DNA of IgG2 type can be performed with a monoclonal primary antibody, such as for example those commercialized by Invitrogen (monoclonal antibodies versus human IgG2—Clone HP6014 provided by InVitrogen Corporation, Camarillo, Calif.) or however polyclonal antibodies able to link to the above antigens.

By following the techniques known to the person skilled in the art for detecting antigens and the antigen-antibody complex, then in a biological sample the levels of IgG2 antibodies, specific for αenolase, annexin AI, complement C1q, histone 2A, 3 and 4 DNA will be determined. In particular, the (primary) antibodies will recognize in a specific way an epitope existing in the described proteins and which in turn can be then recognized by a suitable secondary antibody (anti-human IgG2), directed towards the primary antibody. Such secondary antibody could be marked, for example, with any fluorochrom commonly used in marking secondary antibodies such as, for example, fluorescent substances (by way of illustration: FITC, Cy3, Cy5, Alexa 488, PEe) or enzymes or substances which can be detected by means of enzymatic cytochemistry (for example horseradish peroxidase) to allow then the detection of the primary antibody and then of the antibody anti-αenolase, anti-annexinAI, anti-complement C1q, anti-histone2A, 3 and 4 of IgG2 type.

In exemplifying way, the determination of the antibody anti-αenolase, and however of any antibody of IgG2 type able to recognize the herein described antigens, can be made even by using a proteic array constituted by a solid support whereon different reagents are deposited (in time and logical series) in order to obtain the reaction between antigen and specific antibody (method known as dot-blot). In exemplifying way in case of anti-αenolase IgG2 antibodies, for example, the specific antigen for the anti-αenolase IgG2 antibodies that is αenolase is deposited in known concentrations ("spotted", in technical slang) on solid supports (paper, resins, other supports); in a second passage on the support a complex mixture is deposited, such as for example a cell lysate, a blood or serum sample in order to allow the reaction between antigen and specific antibody existing in the mixture; in a third passage the IgG2 reacting with αenolase by means of anti-human IgG2 antibodies are displayed. Equal methods can be used for the determination of IgG2 antibodies versus annexin AI, complement C1q, histone2A, 3 and 4, DNA.

The determination of the concentration of such antibodies of IgG2 class can be performed, according to what herein described, starting from any biological sample which reasonably comprises the antibody which one wants to detect.

In an embodiment of the invention the biological sample is selected from the group comprising: blood, serum, renal tissue biopsy. Advantageously in a preferred embodiment of the invention, the biological sample is represented by a sample of blood or serum of the examined subject.

According to the type of sample and of the type of technique chosen for determining the concentration of the antibodies of the invention, the person skilled in the art will be able, based upon the common laboratory knowledge, to arrange what is necessary (such as for example sample preparation/processing) in order to perform the herein-described in vitro method.

After determining the concentration of IgG2 antibodies versus at least one of the antigens (anti-αenolase, anti-annexinAI, anti-histone2A, 3 and 4), the subject method provides a passage wherein the concentration determined in the biological sample of the examined subject is compared with a control value. Under control value a reference value related to concentration of IgG2 antibodies for the specific antigen in samples obtained by subjects not having lupus nephritis associated to SLE is meant. Such controls can be chosen for example from the group of: healthy subjects, subjects affected by SLE without LN, subjects affected by nephritis with aetiology different from SLE, such as for example, rheumatoid arthritis.

In a preferred embodiment of the invention, such control value is obtained from samples of healthy subjects or subjects affected by other rheumatic disease (rheumatoid arthritis) or other glomerulonephritis.

As it will be clear to the person skilled in the art, the control value preferably will be the average value of the concentration of IgG2 antibodies able to recognize the herein indicated antigens calculated based upon a group of healthy subjects or subjects affected by other rheumatic and/or renal pathology.

In particular, according to the herein described in vitro method for the prediction and/or the diagnose of lupus nephritis in a subject affected or potentially affected by systemic lupus erythematosus, an increase in the concentration of anti-αenolase and/or anti-annexin AI, and/or anti-complement C1q and/or anti-histone 2A and/or anti-histone 3 and/or anti-histone 4 IgG2 antibodies with respect to the control value indicates a development of lupus nephritis. The antibody quantity for example can be determined as arbitrary unit of optical density expressed as [O.D. unit] corresponding to a determined chemiluminescence signal intensity unit, by way of example, with VersaDoc system equipped with QuantyOne software (Bio-Rad) and it is then calculated and expressed as concentration of the antibody in mg per l (mg/l) of serum by making reference to a standard curve with known content of IgG2. By way of example and absolutely as not limiting, the normal and pathological values related to the concentration of the single auto-antibodies and of the various isotypes can be those shown in FIGS. 3 b-d.

A further subject of the present invention in an in vitro method for diagnose of systemic lupus erythematosus and lupus nephritis in a subject and discriminating them from other rheumatologic conditions and primary glomerular nephritis, said method comprising:

a) determining the concentration of auto-antibodies of IgG2 isotype versus all the antigens selected from the group comprising: αenolase, annexin AI, histone 3, and DNA in a biological sample of said subject and b) comparing the levels of said auto-antibodies with those obtained from a control sample, wherein an increase of the levels of all said auto-antibodies with respect to said control level indicates a development of lupus nephritis.

With respect to the passages during the laboratory determination and to the comparison we remand to what already has been indicated in previous parts of this document.

In Vitro Monitoring Method

The present invention relates even to a method for monitoring the progression of lupus nephritis in a subject affected or potentially affected by systemic lupus erythematosus.

For the definition of "lupus nephritis", "systemic lupus erythematosus" and "potentially affected" see what previously said for the in vitro method for the above prediction and/or the diagnose.

In particular, the monitoring in vitro method comprises the passage of a) determining the concentration of IgG2 antibodies versus at least one of the antigens selected from the group: αenolase, annexin AI, histone 2A, histone 3 and histone 4, DNA, in at least a first and at least a second biological sample of a subject affected or potentially affected by systemic lupus erythematosus, wherein said samples are obtained in different time.

Under the term "monitoring" herein the control of the progression of the pathological status or pathological condition, in this case lupus nephritis, of a patient in time is meant. Therefore, under the term monitoring, in the present invention, performing one or more determinations of the concentration of anti-αenolase, anti-annexinAI, anti-histone 2A, anti-histone 3 and anti-histone 4, anti-DNA IgG2 antibodies in a subject under examination in a certain time interval is designated. By purely way of example and not with limitative purposes, a monitoring can have as aim the evaluation of responsiveness of a subject to a determined therapy, preferably against lupus nephritis. In such optics, then, the determination of anti-αenolase, anti-annexinAI, anti-histone 2A, anti-histone 3 and anti-histone 4, DNA IgG2 antibodies could be for example performed on samples obtained from a given subject affected by LN first, during and/or after a general time interval or therapeutic path. In this case, the possible improvement or worsening or stationarity of the pathological state in the subject method in terms of variation in the concentration of anti-αenolase IgG2 antibodies in the considered time interval corresponds to the possible benefit, or not, of the therapy thereto the subject is submitted.

Even in this case the determination of the concentration of IgG2 antibodies anti-αenolase, anti-annexinAI, anti-histone 2A, anti-histone 3 and anti-histone 4, anti-DNA can be performed starting from any biological sample which reasonably comprises the antibody which one wants to detect. For more detailed information about the biological sample one refers to the analogous section existing in the above in vitro method for the prediction and/or the diagnose of LN. In particular, the biological samples compared for the monitoring, for example, a first and a second sample can be independently chosen from the group comprising: blood, serum, renal tissue biopsy.

Furthermore, the technical aspects related to the methods for determining the concentration of anti-αenolase, anti-annexinAI, anti-histone 2A, anti-histone 3 and anti-histone 4, anti-DNA IgG2 antibody useful to the purpose of the monitoring method, are to be considered analogous to those already described above for the method for predicting and/or diagnosing lupus nephritis.

The determination of the concentration of the antibody of interest to the monitoring purpose should be performed at least in a first biological sample and in at least a second biological sample of a subject obtained at different time, then for example respectively at a time t=0 and t>0. The subject under examination, in particular, can be both a subject submitted to a therapy against lupus nephritis and a subject monitored in time without being necessarily submitted to any type of therapy. In other terms, then, said at least first biological sample obtained at time t=0 can be a sample, for example, before starting the therapy itself, and instead in a subject not submitted to therapy, acquired at a general time t=0. Differently, the second biological sample can be acquired at one or more time intervals starting from said time t=0, therefore defined as time t>0, which by pure way of example can be intervals of hours, days, or months, for example every 15 days. In each case the person skilled in the art, depending upon the subject type and upon the gravity of the pathology, will be able, based upon his/her knowledge, to identify the most suitable time interval to the purpose of herein described monitoring method. Preferably, the first and second sample are respectively obtained before starting a therapy against LN and during and/or after said therapy. Subsequently, the comparison between the concentration of the anti-αenolase IgG2 antibody obtained in said first and said at least second sample will provide information about the progression of the pathological state of the patient.

The variation in the concentration of the antibody of interest, for example anti-αenolase IgG2, is then the instrument allowing to the clinician to evaluate the effectiveness, or not, of the chosen therapeutic strategy. In a particular embodiment an increase in the concentration of IgG2 antibody in the second sample with respect to the first sample indicates the progression of lupus nephritis in a subject affected or potentially affected by systemic lupus erythematosus.

Alternatively, a decrease in the concentration of IgG2 antibodies in the second sample with respect to the first sample designates a non-progression of lupus nephritis in a subject affected or potentially affected by systemic lupus erythematosus.

In particular, the type of therapy to be monitored is a general therapy against lupus nephritis. In particular, the therapy can include treatment with inhibitors of the Angiotensin Converting Enzyme (ACE), high-dosage cortisone, cyclophosphamide, cyclosporine and/or biological therapies (rituximab).

Kit for Predicting and/or Diagnosing Lupus Nephritis and/or for Monitoring a Therapy Against Lupus Nephritis.

A subject of the present invention is also a kit for predicting and/or diagnosing lupus nephritis and/or for monitoring a therapy against lupus nephritis in subjects suffering or potentially suffering from lupus erythematosus comprising.

In particular, such kit comprises at least an aliquot of one or more reagents for the determination of IgG2 antibodies versus at least one of the antigens selected from the group: αenolase, annexin AI, histone 2A, histone 3 and histone 4, DNA in a biological sample of the subject under examination and at least an aliquot of one positive control comprising IgG2 antibodies versus at least one of the antigens selected from the group: αenolase, annexin AI, histone 2A, histone 3 and histone 4, DNA.

In a preferred embodiment of the present invention, said one or more reagents are needed for determining the concentration of anti-αenolase, anti-annexinAI, anti-histone 2A, anti-histone 3 and anti-histone 4, anti-DNA IgG2 antibodies.

Preferably, the kit according to the invention could include at least a primary polyclonal or monoclonal antibody able to recognize such antigens (to be used as standard curve) and, optionally, anti-human IgG2 antibodies. The kit could even include one or more aliquots of a marked or not marked secondary antibody, said secondary antibody being, obviously, specific for the immuno system therefrom the primary antibody used in the standard curve was implemented. Then, if the primary antibody is implemented in mouse, the secondary will be anti-mouse, if implemented in rabbit it will be anti-rabbit and so on. Alternatively, the kit could include a plate thereon there are the dosage theme antigen to allow performing a dosage ELISA.

The kit could additionally include negative controls and/or positive controls. In particular, by purely way of example and not with limitative purpose, the kit can include as positive control the sera of patients (patients could be different) with documented high serum levels of anti-αenolase and/or annexinAI and/or histone2A and/or histone 3 and/or histone 4 IgG2. As positive controls even aliquots of the proteins of interest can be provided, that is αenolase and/or annexinAI and/or histone2A and/or histone 3 and/or histone 4 and/or DNA. As negative control, for example the serum of a pool of patients with known glomerulo nephritis can be used, wherein the antibodies of interest cannot be dosed. In this case negative sera of patients with membraneous glomerulo nephritis will be used. Furthermore, the kit can include suitable reagents and means for the procedure of determining the concentration of anti-αenolase and/or anti-annexinAI and/or anti-histone2A and/or anti-histone 3 and/or anti-histone 4 and/or DNA IgG2 antibodies such as aliquots of buffer solutions, sterile water or other reagents commonly used for detecting, for example, the primary antibody-secondary antibody complex.

The following examples and experimental results have the purpose of designating the ways for implementing the present invention, however without limiting the same.

In a preferred embodiment of the kit, as well as of the method described above, the determination of the concentration of antibodies of IgG2 type able to recognize the antigens chosen from the group: aenolase, annexin A1, histone 2A, histone 3 and histone 4, DNA, is carried out by means of dot-blot or ELISA. Dot-blot. The analysis is performed by using an apparatus for dot-blot of Bio-Rad (Hercules, Calif., USA) and it is based upon the immobilization of the antigen under dosage (aenolase, annexin A1, complement C1 q, histone H2A, H3 and H4) on membrane of nitro-cellulose. The membrane pretreated with TBS is fixed to the apparatus by dot-blot before charging a constant quantity of antigen in TBS (100 ng). The antigen first of all is left in contact for 24 h and then additionally linked to the nitro-cellulose with negative pressure, created with vacuum. The membrane with linked antigens is then saturated in TBS-T (TBS-5% albumin-0.05% gr/v, polyoxyethylene 20 (TWEEN 20) v/v). The serum under dosage dil 1:50 in TBS-T is applied at this point in the wells and left incubating for 6 hours at the environment temperature and then overnight at 4 C; at the end the membrane is washed 3 times in TBS-T. At this point the presence of IgG2 is detected by incubating at the environment temperature, with anti-human IgG2 antibody (Clone: HP6014-InVitrogen Corporation, Camarillo, Calif.) diluted 1:2000 in TBS-T marked with horseradish peroxidase (HPR). After 3 washings wish TBST-T the reaction is developed in chemiluminescence (SuperSignal, West Pico, Chemiluminescent, Thermo scientific, Rockford, USA. A standard curve using IgG2 antibody with different dilutions is prepared to evaluate the reaction linearity and establishing the reading range.

ELISA for determining IgG2 linking the antigens of interest, are placed in the single wells of a plate with 96 wells (MaxiPrep plate 96 wells) and incubated at room temperature for 5 h and then at 4° C. overnight. Aliquots (200 µl) of locking solution (5% BSA in PBS and 0.05% polyoxyethylene 20 (TWEEN 20)) are added in each well, before adding the serum (100 µl) diluted 1:50 in PBS-T (PBS—Tween20 0.05% v/v-BSA 1% gr/v) which is incubated for 4 hours at room temperature and then overnight at 4° C. After 3 washings in PBS-T, with anti-human IgG2 antibodies (Clone: HP6014-InVitrogen Corporation, Camarillo, Calif.) diluted 1:3000 in TBS-T marked with horseradish peroxidase (HPR).

The development of the reaction to peroxidase is obtained by adding 100 µl of substrate $TMB/H_2O_2$ (10:1) and by incubating for variable time depending upon the colorimetric reaction (Mx 30 minutes). Such colorimetric reaction is then locked by adding 100 µl of solution 0.45 M of $H_2SO_4$ and read within 30 min. The absorbance is then read at 450 nm in suitable reader, multiplate reader, iMark (BioRad, Hercules, Calif., USA). A standard curve using IgG2 antibody at different dilutions is prepared for evaluating the reaction linearity and establishing the reading range.

MATERIALS AND METHODS

Patients.

Overall, 216 patients with lupus erythematosus were studied, 103 with LN and 113 with LES without nephropathy. All cases were used for dosing anti-αenolase, anti-annexin AI, and anti histone IgG2. A portion of the same patients with lupus nephritis was studied after an immunosuppressive therapy, that is 6 and 12 months after the beginning of the disease. Renal samples obtained by biopsy from 20 patients were further studied to define the composition of the renal antibodies existing in the kidney (Table 1). In this case the lupus nephritis was defined by known parameters, shown by the literature. The experimental portion on the bioptic samples of frozen kidneys was performed as reported in the subsequent sessions.

Normal Kidneys/Sera.

Biopsies of normal kidneys were obtained from nephroctomies for oncological reasons. Only the portion undamaged by tumural tissue was used in this case. The serum of 134 normal subjects was used to stabilize the normality levels for each single antibody.

Rheumatoid Arthritis.

The serum obtained from 50 patients with rheumatoid arthritis in active phase is used for dosing all antibodies under acute rheumatological conditions.

Other Renal Diseases.

Serum from 278 patients with primitive glomerulonephritis not correlated to lupus was processed as above: 186 were patients with membranous nephropathy, 32 with focal segmental glomerulosclerosis 60 with nephritis of IgA type.

Ethical Committee.

The permission to the study was obtained on Jun. 10, 2010, by the Ethical Committee of San Carlo Borromeo Hospital, Milan (I). The informed consent to the study was obtained from all participants.

Cell Cultures.

Immortalized human podocytes were obtained Dr Saleem (University of Bristol, UK). The cells were kept in RPMI 1640 supplemented with 10% fetal serum (FCS), insulin transferrin, selenium, 100 U/ml penicillin, and 100 mg/ml streptomycin.

Antibodies.

Alpha enolase-1: Rabbit antibodies versus Non-Neuronal Enolase (NNE) (alpha-alpha), AbD Serotec MorphoSys Ltd. (Endeavour House, Kidlington Oxford, UK). Anti-AnnexinA1: Rabbit antibodies versus human annexinAI, Millipore Corp. (Billerica, Mass., USA.). Anti-Histones2A,3,4: Rabbit antibodies versus Histones 2A,3,4, Novus (Biologicals, Cambridge, UK). Anti-C1q. mouse antibodies versus human C1q, Abcam (Cambridge, UK9) Anti-IgG1-IgG2-IgG3-IgG4: monoclonal antibodies versus human IgG1-4 (Clones: HP6070, HP6014, HP6047 and HP6023 respectively for IgG1, IgG2, IgG3 and IgG4) InVitrogen Corporation, (Camarillo, Calif.).

Secondary Antibodies—

Affinity-purified fluorescein isothiocyanate (FITC) F(ab')2 donkey antibodies versus rabbit anti-IgG purified with affinity chromatography and linked to fluorescein thiocyanate (FITC) were all purchased from Jackson Immunoresearch (West Grove, Pa., USA).

Recombinant Proteins.

αenolase: Recombinant, Abnova Corporation (Taipei, Taiwan); AnnexinA1: Recombinant, Creative BioMart, (Shirley, N.Y., USA); Histones: Recombinant, New England BioLabs inc. (Whitby, Canada); C1 q: purified protein, Calbiochem-Merck KG, (Darmstad, Deutschland); DNA: plasmide purified, Invitrogen, (Carlsbad, Calif., USA).

Laser Capture Microdissection (LCM) and Elution of Antibodies from Tissue.

For the microdissection of the glomeruli from the remaining renal tissue a "Laser Capture" technology was used, adapted for frozen tissues. Cryostatic sections (5 µm) of renal tissue were adapted on metal supports coated with thermostated membranes (Molecular Machines & Industries AG; Glattburg, Zurich, Switzerland) and dehydrated by using an Arcturus HistoGene system, LCM Frozen Section Staining Kit (Arcturus Bioscience, Mountain View, Calif.). The glomeruli were identified and isolated with a Molecular Machines & Industries Cellcut LMD system which dissects selectively the Bowman capsule by using the heat generated by a laser source. For each bioptical renal sample, 25 to 30 glomeruli were prepared on the average that are then isolated with special adhesive materials (Nikon Instruments). The elution of immunoglobulins from the isolated glomeruli is made by using saline osmotic gradients.

Two-Dimensional Electrophoresis.

Two dimensional electrophoresis was performed in soft gels of polyacrylamide. The sample preparation provides an initial delipidation in tri-n-butyl-phosphate: acetone: methanol (1:12:1) in ice at 4° C. for 90 min. After centrifugation and washing in the same delipiding solution the not suspended material is centrifuge and dehydrated in air. Before the electrophoretic stroke the sample is dissolved in 7 M urea, 2 M thiourea, 4% (w/v) 3-[3-(cholam idopropyl)-dimethylammonium]-1-propanesulphonate (CHAPS), 5 mM tributyl-phosphine (TBP), 20 mM iodoacetamide (IAA), 40 mM Tris, 0.1 mM ethylene-diamine tetra-acetic acid (EDTA) pH 8.5 and 1% (v/v) thereto a mixture of ampholyte is added containing 60% of pH 3.5-10 and 40% of ampholytes in the pH range of 4-8. The IAA excess is removed chemically by adding dithiothreitol (DTT). In the first electrophoretic dimension strips with pH-gradient of 18 cm; in the second dimension, the proteins are separated based upon their size in 8-16% T gradient polyacrylamide in gels with dimensions 180×160×1.5 mm.

Staining Techniques and Image Analysis.

After separation in SDS-PAGE gels, proteins are visualized by a double staining procedure: in the first phase with methyl-trichloroacetate negative staining followed by Blue silver colloidal Coomassie G250 staining for gels preparing to mass spectrometry. The images from gels are digitalized using a GS800 photometer and acquired with Versa DOC 400. The analysis image is carried out with PD Quest software (Bio-Rad, Hercules, Calif., USA).

Mono-Dimensional Electrophoresis.

Such technique is carried out in slab gel with polyacrylamide gradient according to Laemmli.

Western Blot.

Western blot with glomerular eluates and serum of patients with LN was made by using cell extracts of renal podocyte and mesangial cells. After separation the proteins separated by either mono- or bi-dimensional electrophoresis were transported on nitrocellulose membranes Protean BA (Schleicher & Schuell, Dassel Germany) by using the dedicated apparatus "Novablot semidry system" and by using a continuous gradient buffer system containing 2-amino 2-hydroxymethyl 1,3-propanediol tris 38 mM, glycine 39 mM, sodium dodecyl sulphate (SDS) 0.035% w/v, and methanol 20% v/v. The transfer was performed at 1.55 mA/cm2 for 1.5 h. The serum (0.2 ml diluted in 20 ml TBS) was incubated overnight at room temperature and the membranes were the rinsed in TBS-T 0.15% v/v and incubated with HRP-conjugated anti-human IgG (Invitrogen Corporation, Camarillo, Calif.—2 h, 1:5000).

MALDI-MS.

The proteins purified by two-dimensional gel electrophoresis are rinsed with 50% (v/v) acetonitrile (ACN) in 5 mM ammonium bicarbonate pH 8.9 until full decolouration and then rinsed in 100% (v/v) ACN and in 1 mM CaCl2 and 100 mM ammonium bicarbonate pH 8.9. The enzymatic digestion preparatory to the mass analysis is performed with trypsin in 100 mM ammonium bicarbonate buffer pH 7.8 overnight at 37° C. At the end, the digestion reaction is quenched by the addition of formic acid pH 2. The digested samples first of all are desalted and concentrated with pZipTipC18 column (Millipore, Bedford, Mass., U.S.A.) by using acetonitrile as eluent before MALDI (matrix-assisted laser-desorption ionization)—MS analysis. The peptide mixtures are loaded on MALDI, by using suitable tablets and α-cyano-4-hydroxycinnamic acid as matrix. The analysis is made with Voyager-DE PRO system (Applied Biosystems, Framingham, Mass., U.S.A.). PROWL software is used to identify not ambiguous spots with reference to the National Centre for Biotechnology Information and SwissProt non-redundant sequence databases.

LC-MS.

LC-ESI MS-MS/MS was utilized for characterizing two single proteins (then characterized as vimentin and □enolase). For liquid mass analysis, the proteins initially are treated as for MALDIProtein spots were treated as above. The enzymatic digestion uses trypsin in 100 mM ammonium bicarbonate pH 7.8 overnight at 37° C. The reaction is quenched by the addition of formic acid to pH 2. The used mass spectrometer is a LTQ linear ion trap mass spectrometer (Thermo Electron, San Jose, USA) coupled to a HPLC Surveyor (Thermo Electron) equipped with a Jupiter C18 column 250 mm×1 mm (Phenomenex). The peptides are eluted with acetonitrile gradient (5% B for 6' followed by 5 to 90% B within 109'—eluent A: 0.1% formic acid in water; eluent B: 0.1% formic acid in acetonitrile) at a flow-rate of 50 µl/min. The effluent is directly directed into the electro spray (voltage 5.0 kV) which in turn directs the ions in the capillary at 200° C. and with voltage at 2.85V. MS/MS spectra have a first MS scan (m/z 400-1800) followed by 5 MS/MS analyses. The data acquired by the spectrometer are converted into a file for searching in the dedicated databases (Extract_msn in Bioworks 3.3.1 Sp1 personalized with LTQ spectra). For the protein identification the SEQUEST software 3.3.1 (Thermo Electron) is used, operating on a 10 processor cluster (AETHIA, (Torino, Italia) Turin, Italy). The identity of a single peptide as MS/MS is filtered according to stringent criteria: Xcorr≥1.9 for a single ion, Xcorr≥2.2 for a double-charge ion, and Xcorr≥3.7 for triple-charge ions with probability≤0.01, Delta Cn≥0.1 and Rsp≤4 according to HUPO criteria.

Immunofluorescence on Renal Biopsies.

Renal biopsies in OCT (Tissue Tek, Miles Inc., Elkhart, Ind., USA) are stored in liquid nitrogen. 3-µm sections assembled on glasses treated with poly-L-lysine are processed with immunofluorescence. In a first stage, the renal sections are rinsed in modified Carnoy solution for 10' at 4° C. and subsequently washed in phosphate buffer solution (PBS-pH 7.2). After a washing in bovine albumin serum (BSA) 3% w/v in PBS for 20' at RT, the sections are incubated for 2 h at RT with mono-polyclonal antibodies versus the antigens of interest (for the provenance see section on antibodies) diluted 1:100 in PBS. The reaction development is then made with fluorescein isothiocyanate-conjugated (FITC) specific antibodies. Negative controls were processed in parallel by using PBS or equivalent concentration of not immune rabbit or mouse serum as primary antibody.

Co-Localization of Podocyte Antigens and of Antigens Implanted with IgG2 and Confocal Analysis.

Even for the co-localization studies the renal biopsies treated with OCT (Tissue Tek, Miles Inc., Elkhart, Ind., USA) were stored in liquid nitrogen. Cryosections (3 □M) were fixed in Carnoy solution for 10' at 4° C. and washed in PBS pH 7.2. Not specific interactions were locked by bovine serum albumin (BSA) 3% w/v in PBS for 30' at RT. The sections were then incubated in succession with polyclonal or monoclonal antibodies diluted 1:100 in PBS for 2 h at room temperature. After additional washings, the sections were exposed to Texas Red-conjugate with donkey antibodies versus the rabbit IgG F (ab')2 fragment diluted (1:20) for 1 h at RT. The reaction was then developed with mouse antibodies versus human IgG2 (Invitrogen, Calif.) diluted 1:10 in PBS for 1 h at room temperature. Deposited IgG2 were then displayed with donkey antibodies versus FITC-conjugated mouse IgG (Jackson Immunoresearch, PA) diluted 1:100 for 1 h. The images were analysed by using a confocal microscope (LSM 510 Meta integrated with the Axiovert 200 M inverted microscope Carl Zeiss, Jena Germany) equipped with a 43×/1.30 oil objective.

Characterization of the Isotype and Determination of the Auto-Antibodies in the Glomerular Eluates and in Serum.

Dot-blot. The analysis is performed by using an apparatus for dot-blot of Bio Rad (Hercules, Calif., USA) and it is based upon the immobilization of the dosing antigen (aeolasi, annexin A1, DNA, C1 Q, histone H2A, H3 and H4) on nitrocellulose membrane. The membrane pre-treated with TBS is fixed on the blot-dot apparatus before charging a constant quantity of antigen in TBS (100 ng). During dosage (aeolase, annexin A1, DNA, C1 Q, histone H2A, H3 and H4) 100 µl of this solution are used in the various wells of the system, "multi-well" type, wherein the antigen is at first left in contact for 24 h and then further linked to the nitrocellulose with negative pressure, created with vacuum. The membrane with linked antigens is then saturated in TBS-T (TBS-5% albumin-0.05% gr/v, polyoxyethylene 20 TWEEN 20 v/v). The dosing serum diluted 1:50 in TBS-T at this point is applied in the wells and left to incubate for 6 hours at room temperature and then at 4° C. overnight; at the end the membrane is washed 3 times in TBS-T. At this point the IgG2 presence is detected by incubating at room temperature, with anti-human IgG2 antibodies (Clone: HP6014-InVitrogen Corporation, Camarillo, Calif.) diluted 1:2000 in TBS-T marked with horseradish peroxidase (HPR). After 3 washings with TBST-T the reaction is developed in chemiluminescence (SuperSignal, West Pico, Chemiluminescent, Thermo scientific, Rockford, USA. A standard curve using IgG2 antibodies with different dilutions is prepared to evaluate the reaction linearity and establish the reading range.

ELISA for determining IgG2 of interest in PBS are placed in the single wells of a 9-well plate (MaxiPrep plate 96 wells) and incubated at room temperature for 5 h and then at 4° C. overnight. Aliquots (200 µl) of locking solution (PBS, 5% w/v BSA and 0.05% v/v polyoxyethylene 20 TWEEN 20) were added to each well, before adding the serum (100 µl) diluted 1:50 in PBST (PBS—polyoxyethylene 20 TWEEN 20 0.05% v/v-BSA 1% w/v) which is incubated for 4 hours at room temperature and then at 4° C. overnight. After 3 washings in PBS-T, with anti-human IgG2 antibodies (Clone: HP6014-InVitrogen Corporation, Camarillo, Calif.) diluted 1:3.000 in TBS-T marked with horseradish peroxidase (HPR).

The development of the reaction to peroxidase is obtained by adding 100 µl of TMB/H2O2 substrate (10:1) and incubated for periods of time variable depending upon the colorimetric reaction (mx 30 minutes). Such colorimetric reaction is then stopped by adding 100 µl of 0.45 M solution of H2SO4 and read within 30 min. The absorbance is then read at 450 nm in specific reader, multiplate reader iMark (BioRad, Hercules, Calif., USA). A standard curve using IgG2 antibodies with different dilutions was prepared for evaluating the reaction linearity and establishing the reading range.

Purification of Anti-DNA Antibodies from Serum and Glomerular Eluates.

The purification of anti-dsDNA antibodies from serum of patients with lupus erythematosus and/or from glomerular eluates of patients with lupus nephritis was done with chromatographic technique using cellulose columns with affinity for native DNA (Amersham Pharmacia Biotech.) equilibrated with 25 mM tris-buffer pH 8.0. The protein portion without affinity for DNA were discarded with subsequent washings in PBS whereas the anti-DNA antibodies were eluted with a linear gradient NaCl gradient.

CNBr Digestion of αEnolase and Analysis of Fragmentation Products.

For digestion with cyanogen bromide (CNBr), αenolase (100 µg) was incubated in 0.4 M ammonium bicarbonate with 1% v/v 2-mercaptoethanol at room temperature for 1 h in the dark. Then, the sample was dehydrated with vacuum and resuspended in 5 µL of deionized water, 15 µL of trifluoroacetic acid (TFA) and 5 µL of 5 M CNBr in acetonitrile (ACN); the incubation lasts overnight at 4° C. and the reaction is ended with a new dehydration procedure. The ending sample is resuspended in Tris-HCl 62.5 mM pH 6.8, 2% w/v SDS and 10% glycerol. The analysis of fragments is made in electrophoresis gel in polyacrylamide gradient.

Characterization of the Antigen Recognized by Monoclonal Anti-DNA (IgG2 Clone H147) Derived from Mice with MRL-Ipr/Ipr Spontaneous Lupus.

Anti-DNA antibodies of IgG2 isotype derived from clone (H147) of mice with MRL-Ipr/Ipr spontaneous lupus were provided by Dr Michael Madaio (Georgia Health Sciences University, Augusta, Ga., USA).

Anti-αEnolase IgG Infusion in BALB/c.

Twenty-two BALB/c and six SCID mice were injected intraperitoneum with 1×106 hybridoma cells producing monoclonal anti-αenolase antibodies; hybridoma cells producing IgM anti-DNA antibodies were injected in 3 BALB/c and 2 SCID mice as control. Daily urine collections to determine proteinuria were made up to two weeks, sacrifice date. Histological evaluations of all the renal preparations were evaluated in triplicate by two separate pathologists. All experiments were performed by following NIH criteria for carrying out experiments in laboratory animals.

EXAMPLES

Glomerular eluates from subjects with LN include antibodies recognizing a panel of glomerular antigens. This series of experiments shown in FIG. 1 is preparatory to the diagnostic development which is shown in the patent application. In fact, the concept underlying the patent is that only the antibodies existing in the kidneys of patients with LN (FIG. 1a,b,c,d) and which can be even determined in the serum thereof (FIG. 1e,f) will be pathogenic and thus clinically relevant in the lupus nephritis. The correlation between the presence of the same antibodies in the kidney and in the serum constitutes the logical basis of the finding thereupon the possibility of making early diagnose is based and to prevent the disease by dosing the serum levels thereof (and then in a fluid with easy access). The second logical basis of the finding preparatory to the development of the diagnostic kit is that only the isotypes of the antibodies detectable in the kidney and in the serum of the same patients will have diagnostic value.

For analysing glomerular eluates we utilized biopsies obtained from 20 patients affected by SLE with proteinuria who were submitted to bioptic procedure for diagnostic purposes; most examined patients were already treated with low-dosage steroids or immunosuppressive drugs. The renal tissue obtained by biopsy was frozen according to codified techniques (liquid nitrogen) and glomeruli were then dissected by means of 'laser capture'; immunoglobulins were eluted by isolated glomeruli as stated above and analysed with western-blot techniques (mono and bidimensional electrophoresis) utilizing as fixed antigen cell extracts from podocyte cells, that is the epithelial cells constituting the structural and functional basis of the renal glomerulus.

In order to characterize the proteins recognized by eluted antibodies, first of all we analysed the set of data obtained from samples coming from different LN classes with bi-dimensional electrophoresis. A separate analysis of each sample was then performed by means of mono-dimensional electrophoresis and dot-blot for the selected antigens (FIG. 2). The results from the first approach suggest the presence of various antibodies versus specific proteins that were purified and characterized by Mass spectrometry (LC-MS or MALDI). The same logical procedure and the same techniques were utilized to demonstrate the presence of the same antibodies in the serum of patients under examination with and without LN (FIG. 1e, f). Based upon the presence of antibodies versus specific proteins in the kidney of patients with various LN classes, the preponderance of the antibodies versus α-enolase and annexin AI was defined. These antibodies were characterized in relation to the isotype, the renal co-localization and the positivity in each single biopsy (FIG. 2). In order to verify the entity of the presence of antibodies versus α-enolase and annexin AI, as comparison generical antibodies were considered, by evaluating the presence thereof in the kidney, thereof an increase in the serum of patients with lupus erythematosus is known. Thereamong the presence in the glomerular eluates of antibodies versus DNA (anti-DNA) and versus the proteic constituents of the same (anti-histone) was evaluated; antibodies versus C1q were evaluated too. The target antigens of these antibodies are not present in exposed way in the kidney and therefore they are defined as implantable, that is they can deposit in glomerular loops coming from serum. For each antibody eluted by the kidney (i.e. anti-α-enolase, anti-annexin AI, anti-DNA, anti-Histones and anti C1 q) the specific isotype was characterized and then the frequency of the antibody of the prevailing isotype in each single biopsy and at last the co-localization in the renal glomeruli. In Figure the analyses for the antibodies found versus the proteins expressed by the renal cells (anti-α-enolase and anti-annexin AI) are shown (a,b) and for the implantable antigens (anti-DNA, anti-C1Q, anti-histone2A, 3 and 4) (c, d, e). In all cases all possible isotypes (IgG1, IgG2, IgG3, IgG4) were evaluated with dot-blot and, once determined that for all above antibodies (anti-α-enolase, anti-annexin AI, anti-DNA, anti C1 q, anti-histones2A, 3, 4) the unique isotype was IgG2, personalized dosages were made in all collected biopsies (a-e). The positivity concomitance of the single antibodies in the single biopsies, at last, is shown in (f) which represents graphically as colour scale (heat intensity map) the hierarchical analysis for families of antibodies of IgG2 isotype versus all antigens. The preponderance in the glomeruli of the single patients of antibodies versus αenolase and annexin AI compared to the implanted antigens is clear (in FIG. 2f the colours from grey to black represent high levels of antibody).

After having demonstrated the preponderance of the anti-αenolase and anti-annexin AI IgG2 antibodies (and with minor intensity of anti-DNA, anti-C1Q, anti-histone2A, 3 and 4 antibodies) in the glomeruli of patient with LN, the serum component was evaluated, by characterizing first of all the isotype of the same antibodies and then the circulating levels thereof. In this study portion the antibodies versus αenolase, anti-annexina AI and histones2A, 3 and 4 were focused. In the preparing portion of the experiment the characterization of all prevailing isotypes in serum of antibodies versus all different classes of antigens was made (FIG. 3a). It derives that in serum there is a less isotypical specificity of the antibodies, being able to demonstrate apart from IgG2 (which remains the main isotype) antibodies even of IgG1 and IgG3 isotype. The clinical study related to the circulating levels of all auto-antibodies subject of the research involved 544 patients with different clinical picture, (103 patients with LN, 113 with SLE, 50 with rheumatoid arthritis, 278 with primitive glomerulonephritis, i.e. 60 IgA, 186 membranous nephropathy, 32 with focal glomerulosclerosis focal sclerosis glomerulus) and 130 normal subjects. In a relevant portion of patients with LN the dosages were repeated after 6 months (63) and 12 months (68) of strict immunodepressive therapy and during improvement of inflammation and renal involvement. For the portion on the levels of anti-αenolase IgG2 (FIG. 3b) the dosages were made with dot-blot and compared with ELISA (FIG. 8).

in case of anti-anti-αenolase IgG2, it was demonstrated that the levels are high especially in patients with acute LN with respect to patients with SLE and that such values decrease during the phase of immunosuppressive therapy (FIG. 3c,d). The levels of anti-αenolase IgG2 were found low in patients with rheumatoid arthritis and cannot be wholly dosed in patients with other glomerulonephritis. The ROC curves (FIG. 10) demonstrate high specificity and a sensibility for identifying patients with LN versus all other categories of patients including SLE, rheumatoid arthritis and primitive glomerulonephritis.

In case of anti-annexin AI IgG2 (FIG. 4a,b) increased circulating levels of antibodies in LN versus SLE were demonstrated. The levels decrease with therapy after 12 months (FIG. 4 c).

In case of anti-histone 2A, 3 and 4 antibodies (FIG. 5a,b,c) specific IgG2 levels for all antigens were demonstrated the positivity thereof involves a significant portion of patients. Even in this case the antibody levels were significantly higher in patients with LN versus other groups (SLE, RA, other glomerulonephritis) but the levels were lower by about one-two orders of magnitude with respect to the anti-αenolase IgG2 (0.5 mg/l vs 40 mg/l). In case of anti-histones 2a antibodies (a) an increase in antibodies of IgG1 and IgG3 class is also present, even if positivity involves a less important portion of patients.

In FIG. 11, a hierarchical analysis (Heat Map) is shown related to the contribution given by each specific antibody in identifying patients belonging to the different studied groups. It is evident that the presence of high serum levels of anti-αenolase and anti-annexin AI IgG2 identify in very clear manner patients affected by SLE with and without nephropathy (in dark) from patients affected by rheumatoid arthritis (in light); high levels of anti H3e IgG2 and anti-DNA IgG3 contribute significantly to identify patients with SLE but they are not sensible to identify patients with rheumatoid arthritis. On the whole the dosage of all antibodies described herein allows differentiating the various sub-groups and mainly the patients with SLE, with SLE and associated nephropathy, from patients with rheumatoid arthritis and obviously the normal controls.

The last part of the study was dedicated to verify specificity of anti-αenolase IgG2 antibodies for the lupus nephritis and to define even the implications thereof in the disease animal models. The results related to specificity are shown in FIG. 6. The reactivity of antibodies of IgG2 isotype purified by serum of patients with membranous nephropathy, a category of patients who were recently recognized to have high levels of anti-αenolase IgG4 in the glomeruli and serum. The specificity was evaluated by using fragments of αenolase obtained with CNBr (a). The results showed that IgG2 and IgG4 recognized different peptides derived from CNBr fragmentation, that is respectively the products with 1.3 KDa and 6.8 kDa. The results of the experiments made to highlight homologies between human lupus nephropathy and the mouse one. They are shown in FIG. 6d and in FIG. 9. In the first case the antibodies responsible for the nephropathy characteristic of the mouse predisposed to lupus (MRL-Ipr/Ipr) were characterized. In this model the experimental lupus nephropathy is reproduced by means of infusion of monoclonal antibodies anti-DNA IgG2 produced by cells derived from subject mice. The prototype of such antibody which is produced by the clone H147 (an IgG2 codified by 7183/81X VHgene) induces the formation of glomerular and tubular basal membrane formation, mesangial immune deposits and proliferative glomerulonephritis after the passive transfer to normal mice. The target antigen of these antibodies has been recognized to be αenolase (FIG. 6d). Therefore herein it is demonstrated that αenolase is recognized by the nephritogenic antibodies derived from mice predisposed to lupus.

In a second set of experiments it was confirmed that anti-αenolase IgG2 can induce lupus nephritis in experimental animals. The experiment was performed in 22 BALB/c mice which were injected intra-peritoneally hybridomas producing anti-αenolase IgG antibodies or anti-dsDNA IgM antibodies as negative control. Proteinuria (100-300 mg %) was found in 25% of injected mice after 10 days from injection (FIG. 9a); proteinuria in checking mice was constantly lower than 10 mg %. The renal hystological analysis showed proliferative glomerular lesions in 5 mice out of 22 injected with anti-αenolase monoclonal antibodies (b), in 2 mice proliferative lesions coexisted with thickening of basal membrane and in 2 with tubular infiltrates (c). In six SCID mice injected in similar way with the hybridomas: 4 developed glomerular proliferative lesions with halfmoons and tubulo-interstitial infiltrates (c). The mice injected with monoclonal anti-DNA IgM developed only focal glomerular infiltrates.

Taken together, the results of the experiments made in animals are to be considered a support of the concept that anti-αenolase IgG2 are toxic for the kidney and then the high level thereof found in subjects with lupus nephritis finds a direct justification in the disease pathogenesis.

The invention claimed is:

1. An in vitro method for diagnosing lupus nephritis in a subject affected by systemic lupus erythematosus, comprising the following steps:

a) determining the concentration of immunoglobulin G2 (IgG2) antibodies that specifically bind at least one of the antigens selected from the group consisting of: alpha-enolase, annexin AI, histone 2A, histone 3, histone 4, and deoxyribonucleic acid (DNA) in a biological sample of said subject;

b) comparing said antibody concentrations in said biological sample with a control value, wherein the control value is the antibody concentration in a normal subject; and wherein an increase of the concentration of said antibodies with respect to said control value indicates a development of lupus nephritis; and c) further comprising administering a general therapy against lupus nephritis selected from an angiotensin converting enzyme (ACE) inhibitor, high-dosage cortisone, cyclophosphamide, cyclosporine, or a biological therapy to subjects having an increased antibody concentration compared to a control value.

2. The method according to claim 1, wherein said biological sample is selected from the group consisting of: blood, serum, and renal tissue biopsy.

3. The method according to claim 1, wherein said determination is carried out by ELISA (enzyme-linked Immunoabsorbent assay), dot-blot, western-blot, RIA (radioimmunoassay), immunochemistry, or mass spectrometry.

4. An in vitro method for monitoring progression of lupus nephritis in a patient affected by systemic lupus erythematosus, comprising the following steps:

a) determining the concentration of immunoglobulin G2 (IgG2) antibodies that specifically bind at least one of the antigens selected from the group consisting of: alpha-enolase, annexin AI, histone 2A, histone 3, histone 4, and deoxyribonucleic acid (DNA) in at least a first and at least a second biological sample of said subject, wherein said at least a first and a second samples obtained at different times; and b) comparing the antibody concentration obtained for said first and second sample; and c) administering a general therapy against lupus nephritis selected from an angiotensin converting enzyme (ACE) inhibitor, high-dosage cortisone, cyclophosphamide, cyclosporine, or a biological therapy.

5. The method according to claim 4, wherein said at least a first and second sample are respectively obtained before starting a therapy and during and/or after said therapy.

6. The in vitro method according to claim 5, wherein an increase in the concentration of said antibodies in said second sample with respect to said first sample indicates the progression of lupus nephritis in said subject.

7. The in vitro method according to claim 5, wherein a decrease in the concentration of said antibodies in said second sample with respect to said first sample designates a non-progression of lupus nephritis in said subject.

8. The method according to claim 4, wherein said first and/or second sample are independently selected from the group consisting of: blood, serum, and renal tissue biopsy.

* * * * *